(12) United States Patent
Guiot et al.

(10) Patent No.: US 7,682,815 B2
(45) Date of Patent: Mar. 23, 2010

(54) BIOELECTROLYTICAL METHANOGENIC/METHANOTROPHIC COUPLING FOR BIOREMEDIATION OF GROUND WATER

(75) Inventors: Serge R. Guiot, Montreal (CA); Boris Tartakovsky, Cote-St-Luc (CA)

(73) Assignee: National Research Council of Canada, Ottawa, Ontario (CA)

(*) Notice: Subject to any disclaimer, the term of this patent is extended or adjusted under 35 U.S.C. 154(b) by 545 days.

(21) Appl. No.: 11/597,662

(22) PCT Filed: May 25, 2005

(86) PCT No.: PCT/CA2005/000793

§ 371 (c)(1),
(2), (4) Date: Nov. 24, 2006

(87) PCT Pub. No.: WO2005/115930

PCT Pub. Date: Dec. 8, 2005

(65) Prior Publication Data

US 2007/0218540 A1    Sep. 20, 2007

Related U.S. Application Data

(60) Provisional application No. 60/574,229, filed on May 26, 2004.

(51) Int. Cl.
*B09B 3/00* (2006.01)
(52) U.S. Cl. .................................. 435/262.5
(58) Field of Classification Search ............. 435/262.5; 210/611
See application file for complete search history.

(56) References Cited

U.S. PATENT DOCUMENTS

| | | | | |
|---|---|---|---|---|
| 5,599,451 A | * | 2/1997 | Guiot | 210/605 |
| 5,919,351 A | * | 7/1999 | Rijnaarts et al. | 205/701 |
| 6,391,184 B1 | * | 5/2002 | Orolin et al. | 205/687 |
| 6,610,178 B2 | * | 8/2003 | Kato et al. | 204/158.21 |
| 6,878,856 B2 | * | 4/2005 | Kim et al. | 588/319 |

OTHER PUBLICATIONS

Tartakovsky B. et al. Tetrachloroethylene Dechlorination Using a Consortium of Coimmobilized Methanogenic and Methanotrophic Bacteria. Enzyme and Microbial Technology 22(4)255-260, 1998.*
Tartakovsky B. et al. Trichloroethylene Degradation in a Coupled Anaerobic/Aerobic Reactor Oxygenated Using Hydrogen Peroxide. Environmental Science Technology 37(24)5823-5828, Dec. 15, 2003.*
Tartakovsky B. et al. Degradation of Trichlroethylene in a Coupled Anaerobic/Aerobic Bioreactor. Biochemical Engineering J 26(1)72-81, 2005.*

* cited by examiner

*Primary Examiner*—Ralph Gitomer
(74) *Attorney, Agent, or Firm*—Hans Koenig

(57) ABSTRACT

The invention disclosure is a method of bioremediation of wastewater, particularly groundwater, by utilizing coupled anaerobic and aerobic biological treatment, more specifically, methanogenic (strictly anaerobic) and methanotrophic (strictly aerobic) microbial populations, in combination with a supply of in-situ generated water-dissolved oxygen and hydrogen. Water electrolysis is used to produce water-dissolved oxygen and hydrogen. The immediate advantage of using $H_2$ from the electrolysis is to provide electron donors to methanogens to reductively dechlorinate the chloroaliphatics, and to reduce the water carbonates and generate methane which is used as energy and carbon source for the methanotrophic bacteria. Oxygen is used as electron acceptor by the aerobic bacteria, including the methanotrophs. The addition of an organic carbon source can be minimized or even eliminated, so as to diminish the competition between methanotrophic bacteria and heterotrophic bacteria for oxygen.

10 Claims, 13 Drawing Sheets

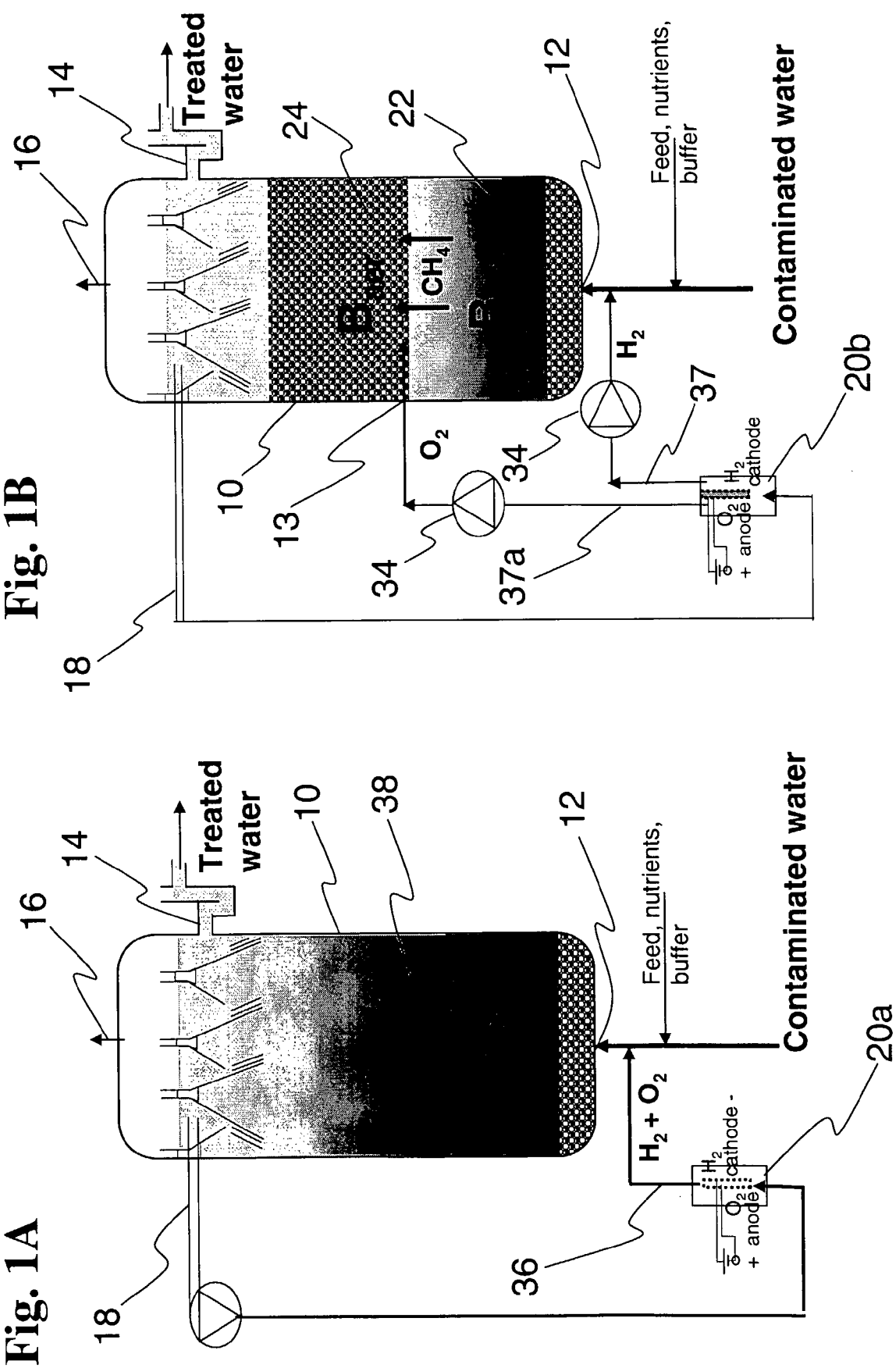

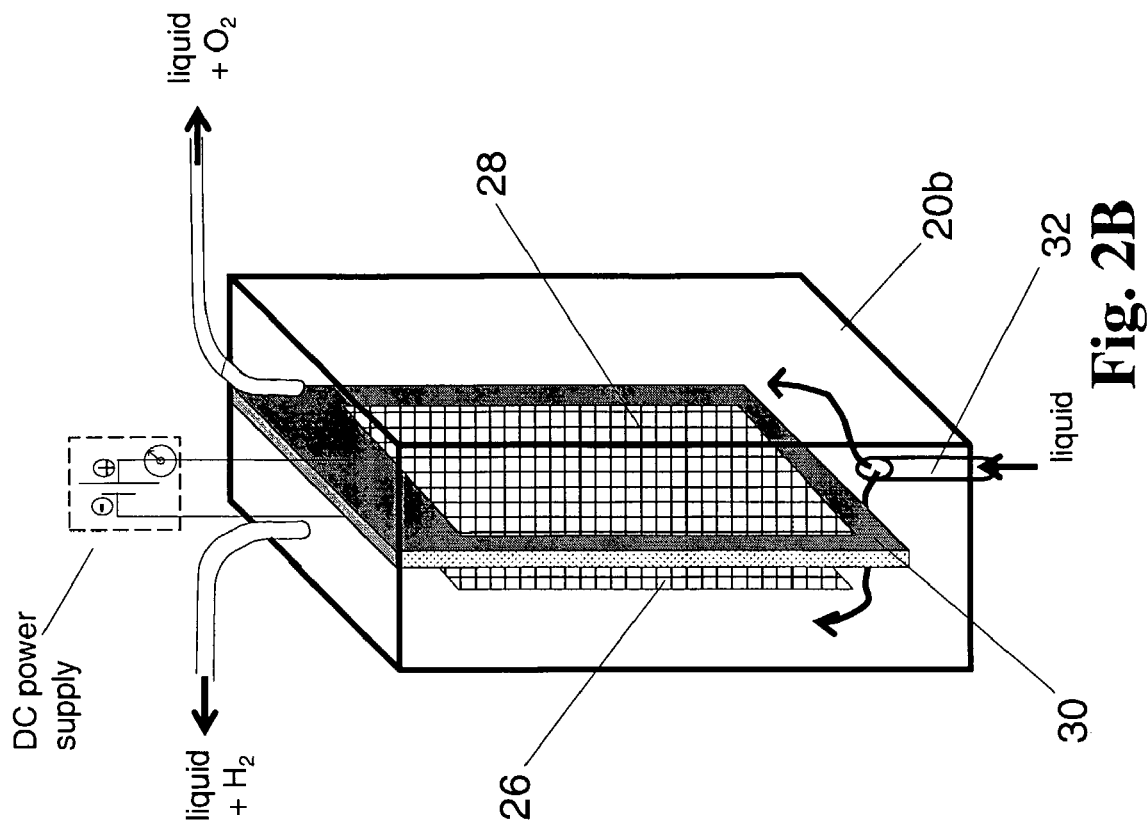
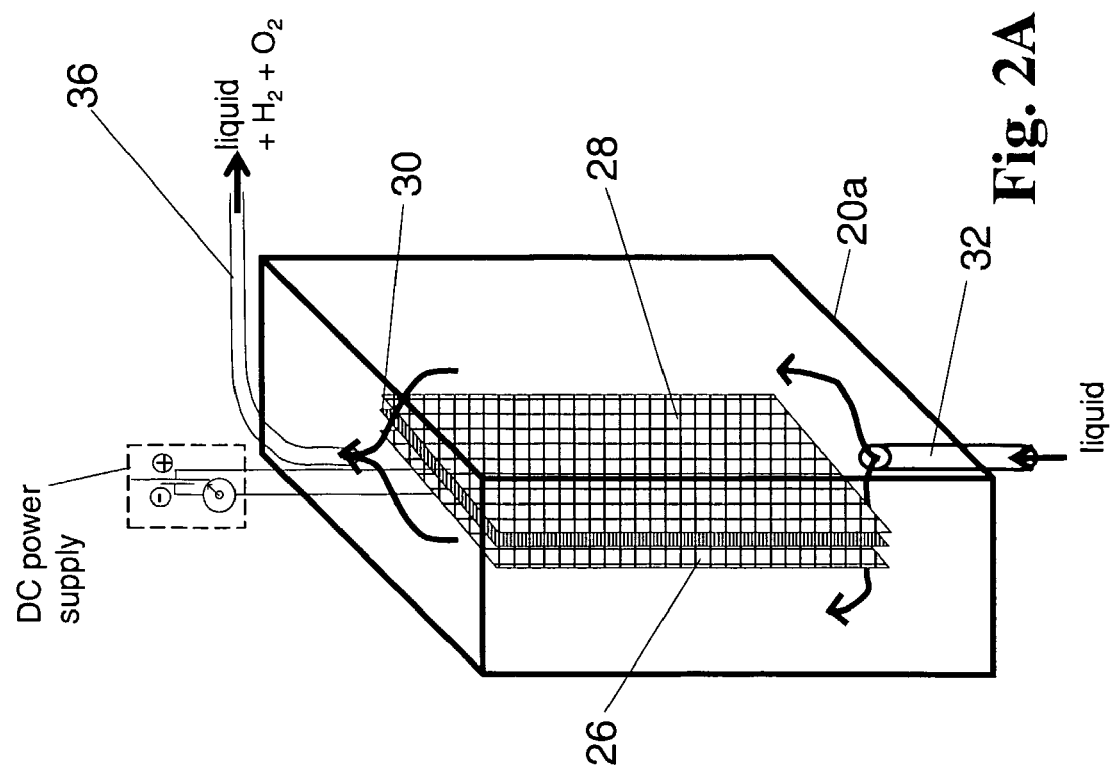

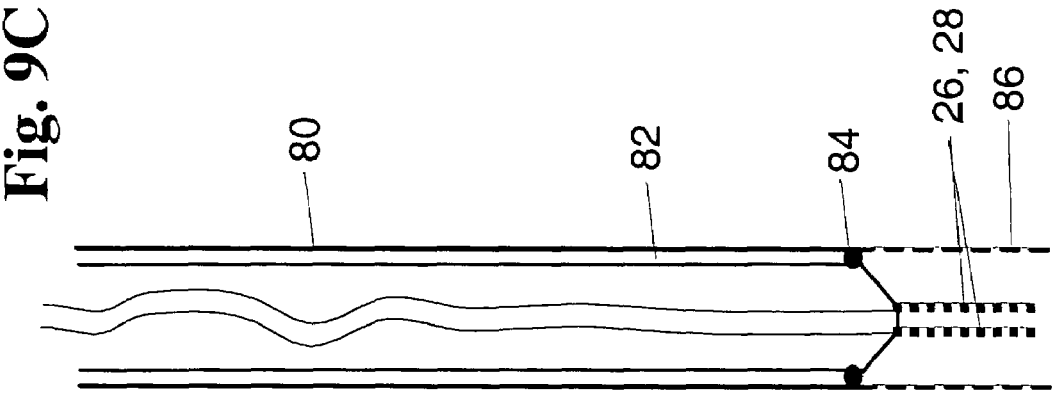
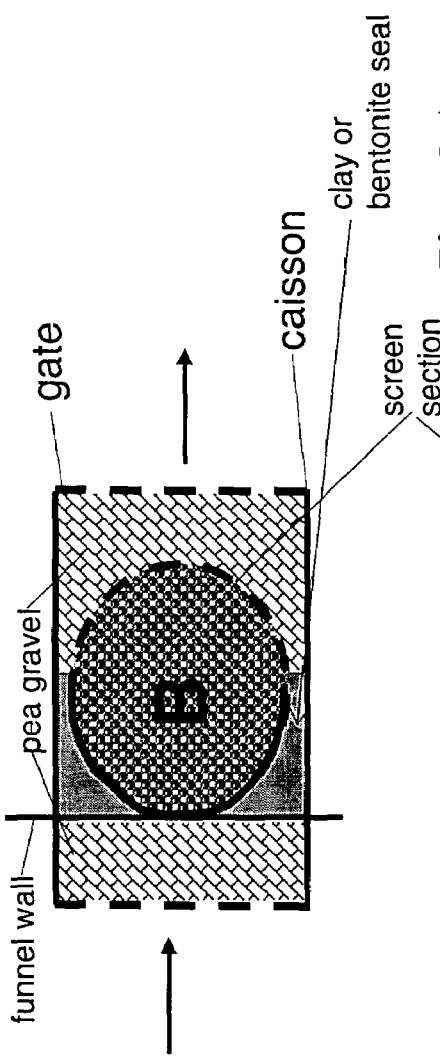
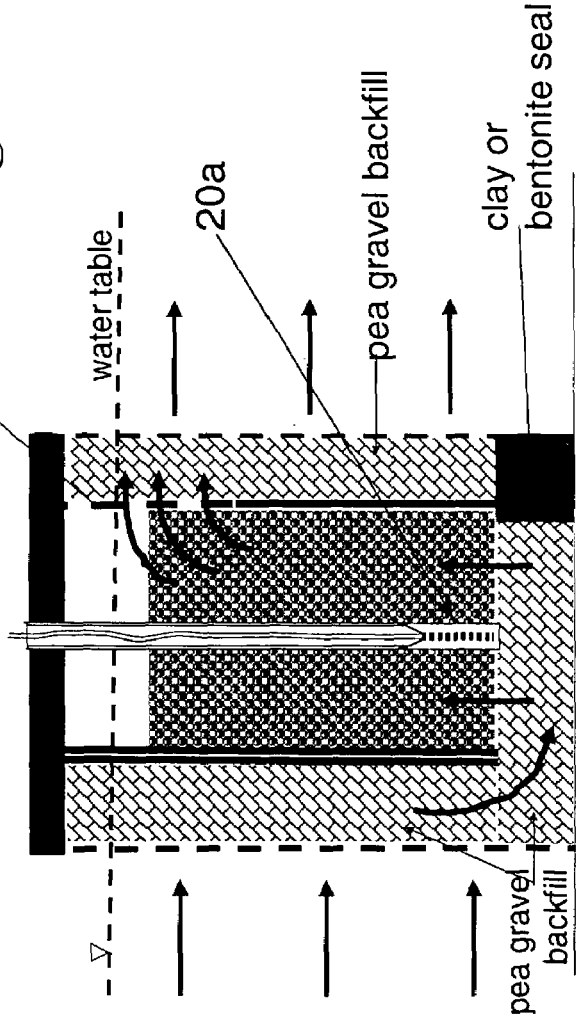

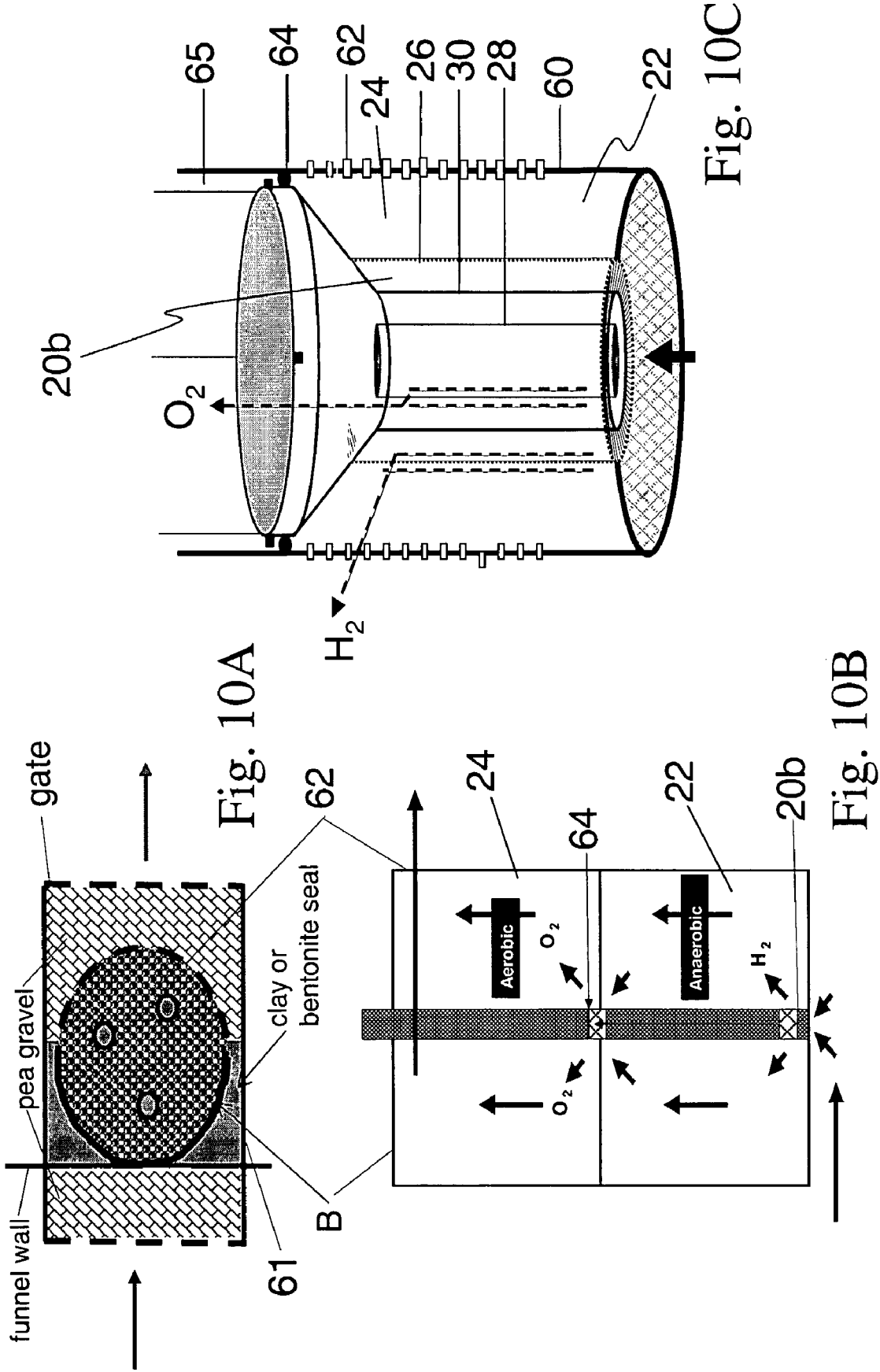

BIOELECTROLYTICAL METHANOGENIC/METHANOTROPHIC COUPLING FOR BIOREMEDIATION OF GROUND WATER

This application is a National Stage application of PCT Application PCT/CA2005/000793 filed May 25, 2005 which claims benefit of U.S. Provisional Application 60/574,229 filed May 26, 2004.

BACKGROUND OF THE INVENTION

This invention relates to the remediation of contaminated aquifers (groundwater). Chlorinated aliphatics such as tetrachloroethylene or perchloroethylene (PCE), trichloroethylene (TCE), trichloroethane (TCA) and dichloroethylene (DCE) have become common pollutants of soil and groundwater in North America. In the case of TCE this was due to its extensive use as a solvent and degreasing agent in industry, and to spills caused by mishandling, accidental or otherwise. The removal of PCE and TCE from soils and groundwater is an important environmental issue, especially since PCE, TCE and derivatives are potentially toxic to human beings and other life-forms. The invention relates also to other emergent contaminants, such as chloropropanes, namely 1,2,3-trichloropropane (TCP).

Currently, there are several approaches for the biodegradation of chlorinated compounds.

Biodegradation of chlorinated compounds can be accomplished by aerobic microorganisms, namely by methanotrophs or other microorganisms possessing mono-oxygenases with broad selectivity. Aerobic microorganisms (in particular methanotrophs) are capable of efficient mineralization of low chlorinated compounds, while the biodegradation rates of highly chlorinated compounds under aerobic conditions are lower. Moreover, most highly chlorinated chemicals are refractory to conventional aerobic conditions. Polychlorobiphenyls (PCB) such as pentachlorobiphenyl, highly chlorinated monoaromatics such as hexachlorobenzene and 1,2,4,5-tetrachlorobenzene, chlorinated aliphatics such as hexachlorobutadiene, PCE and carbon tetrachloride ($CCl_4$), hetero-substituted aromatics such as 4-chloro-2-nitrophenol (CNP) are not appreciably or not degraded at all under conventional aerobic conditions (Brown et al. 1987; Janssen et al. 1991; Zitomer and Speece 1993; Galli and McCarty 1989; Beunink and Rehm 1990; Field et al. 1995).

Biodegradation of chlorinated compounds can also be accomplished by reductive dechlorination i.e. by anaerobic bacteria e.g. methanogens, which chlorinated compounds. Although the rate of dechlorination of the contaminant itself could be sufficiently high, it decreases with decreasing extent of halogenation (Mohn and Tiedje 1992). Consequently, anaerobic degradation of chlorinated compounds often is incomplete and results in the production of less chlorinated intermediates. These intermediates can be even more toxic than the initial compound. For instance reductive dechlorination of PCE stalls at cis-dichloroethene (cDCE). To date, only one microorganism, *Dehalococcoides ethenogenes*, has been shown to dechlorinate PCE, TCE or DCE to ethene (Major et al. 2003).

Accordingly, complete biodegradation of these compounds often requires a combination of anaerobic and aerobic conditions. Sequential anaerobic and aerobic biodegradation carried out in two reactors has been demonstrated. It provides complete mineralization of the initial compound. However, the existence of two bioreactor systems (anaerobic and aerobic) increases the cost. As well, a supply of methane is required if the aerobic part is based on methanotrophic activity.

For groundwater applications, reductive dechlorination of PCE or TCE tends to be incomplete while aerobic degradation of TCE occurs in narrow ecological zones due to its specific requirements. In general, anaerobic activity is confined to the centers of contaminant plumes which are usually anaerobic, and aerobic activity occurs at the edges of the plumes where oxygen is present.

Moreover, in view of the low solubility in water of methane (which is required as a carbon source for the methanotrophs), it is difficult to inject enough methane into the system to support sufficient metabolism of the methanotrophs.

An example of a prior art approach is found in U.S. Pat. No. 6,391,184. This patent reports methods for in-situ decontamination of groundwater by producing high amounts of dissolved oxygen and reactive initiators such as hydroxyl radicals. An electrolysis apparatus is described such as to effect the water electrolysis at given depth in screened wells. The apparatus essentially is a probe incorporating a submersible pump, an electrolysis cell, a chlorine filter and distribution chamber. The probe can be introduced into and removed from the well. The incorporation of a pumping device at the probe tip allows for turning the well into a reactive well. The method also includes a protocol to position the wells given the hydrogeology of the site and the extension of its contamination, as well as an on-line control strategy to properly command the pumping and electrolysis operation.

However, there is no use that is recognized for hydrogen. The method is essentially an alternative to air sparging, with much higher efficiency in terms of oxygen transfer to the liquid phase (resulting in higher dissolved oxygen concentration and better diffusion), and with the additional benefit of hydroxyl radicals generation. The outcomes expected are an initiation of chemical oxidation and a stimulation of aerobic indigenous microbial populations (oxidative pathways).

In another prior art, U.S. Pat. No. 5,919,351, the patent uses in-situ electrolysis with two flat screened electrodes placed perpendicular to the water flow direction, and crossed by the water path. First electrode is negative (cathode) and generates hydrogen; second one is positive (anode) and generates oxygen. This creates two zones, anaerobic and aerobic, so that the treatment is sequential rather than simultaneous coupling due to the oxygen gradient across the biofilm. In addition, the distance between the electrodes is relatively large, in the meter range, so that high voltage has to be applied for enough current to be generated. In addition, water has to flow across the flat screened electrode, requiring large electrode areas, and a risk of electrode clogging, i.e. loss of electrolytical efficacy and permeability. Those characteristics jeopardize the cost-effectiveness of the system, further to the fact that this method is limited to shallow aquifers.

An integrated anaerobic and aerobic system for bioremediation of groundwater is described in our previous U.S. Pat. No. 5,599,451, the disclosure of which is incorporated herein by reference (Guiot 1997a). Although this system has been found to be quite useful for a variety of applications and compounds (Guiot 1997b, Tartakovsky et al. 2001), the low solubility of oxygen in water and low density of biomass granules cause certain problems.

SUMMARY OF THE INVENTION

According to the present invention, a bioremediation method and apparatus is provided, which involves a combination of anaerobic and aerobic metabolisms, fueled by water electrolysis, with an intrinsic source of carbon source (water dissolved methane) for the methanotrophs.

According to one aspect of the invention, it is proposed to combine the advantages of reductive/oxidative degradation mechanisms using anaerobic and aerobic coupling, more precisely methanogenic/methanotrophic coupling (MAMOC), in a single biofilm system (FIGS. 1a, 2a and 4).

According to another aspect of the invention, a solution for the oxygen supply problem is provided, by using water electrolysis. In an embodiment, by using an electrolytic cell for the oxygenation of the contaminated liquid to be treated, one can also benefit from the hydrogen produced at the same time. The electrolytic cell is placed in the system recirculation line. The circulating contaminated liquid flows through the electrolytic cell which is thus continuously enriched in both $H_2$ and $O_2$. This results in a fully integrated (or single-stage) bioelectrolytic methanogenic/methanotrophic coupled (eMAMOC) system.

An immediate advantage of using intrinsic $H_2$ from the electrolysis, is not to depend on an organic carbon-source for the methanotrophs, and for the electron donors for both reductive dechlorination and methane production from carbonates (providing the medium is carbonated enough) by methanogens. Methane is then used as energy and carbon-source by methanotrophic bacteria, and oxygen from the electrolysis, is also used by methanotrophic bacteria as electron acceptor. Methanotrophs can also complete the degradation by oxidizing the intermediates partially reductively dechlorinated by methanogens. This forms thus, a system made of biological components in synergism (mutualism).

In another embodiment of the invention, an alternative scheme for implementing the bioelectrolytic methanogenic/methanotrophic coupling (eMAMOC) is proposed. This scheme considers a different bioreactor configuration (FIGS. 1b and 2b). The methanogenic zone is in the lower part of the biosystem, and the methanotrophic zone, in the upper part of the system, i.e. a dual system is used. As the methanotrophic zone superimposes the methanogenic zone and because of the fluid continuity between the two compartments, the methane produced in the methanogenic compartment is allowed to rise and freely pass to and feed the methanotrophic compartment. Simultaneously, compounds partially dechlorinated in the methanogenic compartment are transported by the liquid upward flow to the methanotrophic compartment. The $H_2$- and $O_2$-enriched liquid fluxes are dissociated accordingly, by duplicating the liquid recirculation lines out of the electrolytic cell i.e. to separately provide $H_2$ to the methanogenic compartment, an $O_2$ to the methanotrophic compartment. The spatial distance between the methanogenic and methanotrophic populations does not allow the close synergism that we have in the single-stage system. However this is a more straightforward method for facilitating the methanotrophs proliferation.

It will be apparent to those skilled in the art that the electrolytic integrated methanogenic/methanotrophic coupled biosystem for biotreatment of contaminated liquid (water) may have several fields of application. Although applicable to chlorinated aliphatics contamination in groundwater (through either ex situ or in situ treatment), it will be appreciated that such biosystem concept could also be applied to any contaminant requiring reductive and oxidative steps for its biodegradation. This may include contaminants in groundwater and wastewater such as polychlorinated aromatics (chlorophenols, chlorobenzenes, polychlorinated phenyls, chloro-lignins, . . . ), compounds substituted with nitro-groups (TNT, nitrocellulose, RDX, HMX, NDMA . . . ), azo-organic compounds such azo-dyes, . . . . Technologies based on such concept could also be applied to nitrification-denitrification of effluents and groundwater, considering electrolytic oxygen would be used for the nitrification step, while the electrolytic hydrogen would be used for the denitrification steps, as the electron donor for reducing nitrate and nitrite into nitrogen. In some of those applications, this means that, if the methanotrophic activities might not be instrumental and required, they should be substituted with other aerobic activity, for instance in the treatment of nitrogen pollution, aerobic populations would be ammonium-oxidizing bacteria.

According to one aspect of the invention, a method is provided for the continuous synchronous bioremediation of an aqueous contaminated liquid including a contaminant requiring reductive and oxidative steps for its biodegradation, comprising (a) providing a bioreactor containing a coupled single phase anaerobic (methanogenic) aerobic (methanotrophic) biofilm, said biofilm comprising an anaerobic (methanogenic) zone located at a central core area of the biofilm, and a juxtaposed aerobic (methanotrophic) zone at a surrounding peripheral area of the biofilm, in fluid communication with the anaerobic (methanogenic) zone, and including a decreasing gradient of oxygen concentration from the aerobic (methanotrophic) zone to the anaerobic (methanogenic) zone toward the core area, and an electrolytic cell for hydrolyzing water, in fluid communication with the bioreactor, (b) circulating the contaminated liquid through the electrolytic cell to together introduce a controlled amount of dissolved oxygen and hydrogen into the contaminated liquid, and (c) continuously cycling the oxygenated and hydrogenated contaminated liquid through the bioreactor, wherein dissolved hydrogen is used as an electron donor by methanogenic bacteria and to in situ generate methane, and by anaerobic bacteria including methanogens and dissolved oxygen is used as an electron acceptor by aerobic including methanotrophic bacteria, and methane is used by methanotrophic bacteria, to remediate the contaminated liquid, respectively by reductive and oxidative steps.

According to another aspect of the invention, a method is provided for the continuous synchronous bioremediation of an aqueous contaminated liquid including a contaminant requiring reductive and oxidative steps for its biodegradation, comprising (a) providing a bioreactor containing a coupled dual phase anaerobic (methanogenic) aerobic/methanotrophic biofilm, said biofilm comprising an aerobic (methanotrophic) zone in fluid communication with and superimposing an anaerobic (methanogenic) zone, and including a decreasing gradient of oxygen concentration from the aerobic (methanotrophic) zone to the anaerobic (methanogenic) zone, and an electrolytic cell for hydrolyzing water, in fluid communication with the bioreactor, (b) circulating the contaminated liquid through the electrolytic cell to separately introduce a controlled amount of dissolved oxygen and hydrogen into the contaminated liquid, and providing dissolved oxygen to the aerobic (methanotrophic) zone and dissolved hydrogen to the anerobic (methanogenic) zone, and (c) continuously cycling the oxygenated and hydrogenated contaminated liquid through the bioreactor, wherein dissolved hydrogen is used as an electron donor by methanogenic bacteria and to in situ generate methane, and by anaerobic bacteria including methanogens; and dissolved oxygen is used as an electron acceptor by aerobic, including methanotrophic bacteria, and methane is used by methanotrophic bacteria, to remediate the contaminated liquid, respectively by reductive and oxidative steps.

According to yet another aspect of the invention, an apparatus is provided for the continuous synchronous bioremediation of an aqueous contaminated liquid including a contaminant requiring reductive and oxidative steps for its biodegradation, comprising (a) a bioreactor containing a coupled single phase anerobic (methanogenic)/aerobic (methanotrophic) biofilm, said biofilm comprising an anaerobic (methanogenic) zone located at a central core area of the biofilm, and a juxtaposed aerobic (methanotrophic) zone at a surrounding peripheral area of the biofilm, in fluid communication with the anaerobic (methanogenic) zone, and including a decreasing gradient of oxygen concentration from the aerobic (methanotrophic) zone to the anaerobic (methanogenic) zone toward the core area, (b) inlet means in said bioreactor for influent contaminated liquid, (c) first outlet means in said bioreactor for effluent treated liquid, (d) second outlet means in said bioreactor for effluent gas, (e) conduit means outside of said bioreactor for connecting said inlet and said first outlet means to define a closed loop including said bioreactor, (f) an electrolytic cell for hydrolyzing water associated with said conduit means for together introducing oxygen and hydrogen into said conduit means, whereby a controlled amount of oxygen and hydrogen is dissolved in said liquid outside of said bioreactor, and (g) pump means for continuously cycling contaminated liquid through the apparatus, wherein dissolved hydrogen is used as an electron donor by methanogenic bacteria and to in situ generate methane, and by anaerobic bacteria, including methanogens; and dissolved oxygen is used as an electron acceptor by aerobic, including methanotrophic bacteria, and methane is used by methanotrophic bacteria, to remediate the contaminated liquid, respectively by reductive and oxidative steps.

According to a further aspect of the invention, an apparatus is provided for the continuous synchronous bioremediation of an aqueous contaminated liquid including a contaminant requiring reductive and oxidative steps for its biodegradation, comprising (a) a bioreactor containing a coupled dual phase anaerobic (methanogenic)/aerobic (methanotrophic) biofilm, said biofilm comprising an aerobic (methanotrophic) zone in fluid communication with and superimposing an anaerobic (methanogenic) zone, and including a decreasing gradient of oxygen concentration from the aerobic (methanotrophic) zone to the anaerobic (methanogenic) zone, (b) inlet means in said bioreactor for influent contaminated liquid, (c) first outlet means in said bioreactor for effluent treated liquid, (d) second outlet means in said bioreactor for effluent gas, (e) conduit means outside of said bioreactor for connecting said inlet and said first outlet means to define a closed loop including said bioreactor, (f) an electrolytic cell for hydrolyzing water associated with said conduit means for separately introducing oxygen and hydrogen into said conduit means, whereby a controlled amount of oxygen and hydrogen is dissolved in said liquid outside of said bioreactor, and (g) pump means for continuously cycling contaminated liquid through the bioreator, wherein dissolved hydrogen is used as an electron donor by methanogenic bacteria and to in situ generate methane, and by anaerobic bacteria including methanogens; and dissolved oxygen is used as an electron acceptor by methanotrophic bacteria, and methane is used by methanotrophic bacteria, to remediate the contaminated liquid, respectively by reductive and oxidative steps.

BRIEF DESCRIPTION OF THE DRAWINGS

FIG. 1 Schematics of bioelectrolytic methanogenic/methanotrophic coupling (eMAMOC) within a bioreactor system according to the invention (a) single-stage, (b) dual stage FIG. 2. Schematics of the electrolytic cell (a) single chamber, with one outlet for mixed $H_2$ and $O_2$ enriched liquid; (b) double chamber, for two outlets and separate $H_2$ and $O_2$ enriched liquids.

a, funnel; b, gate; c, crib; d, removable bioactive cassette; e, pea gravel backfill; f, water flow direction; g, extraction well; h, reinjection well; m, monitoring wells; EC, electrolysis cartridge.

FIG. 9. Example of completely passive application. Details of a single bioreactive element (cassette) with a cylindrical shape, within a rectangular crib (a, top view; b, vertical cross section; c, detail of the removable passive electrolytical device) according to the invention.

FIG. 10. Example of completely passive application, for the case of the dual zone system. Details of a single bioreactive element (cassette) with a cylindrical shape, within a rectangular crib: (A) top view, with a set of 3 wells; (B) vertical cross section (only one well is drawn); (C) detail of the removable passive electrolytical device (probe), according to the invention.

Figure 11:
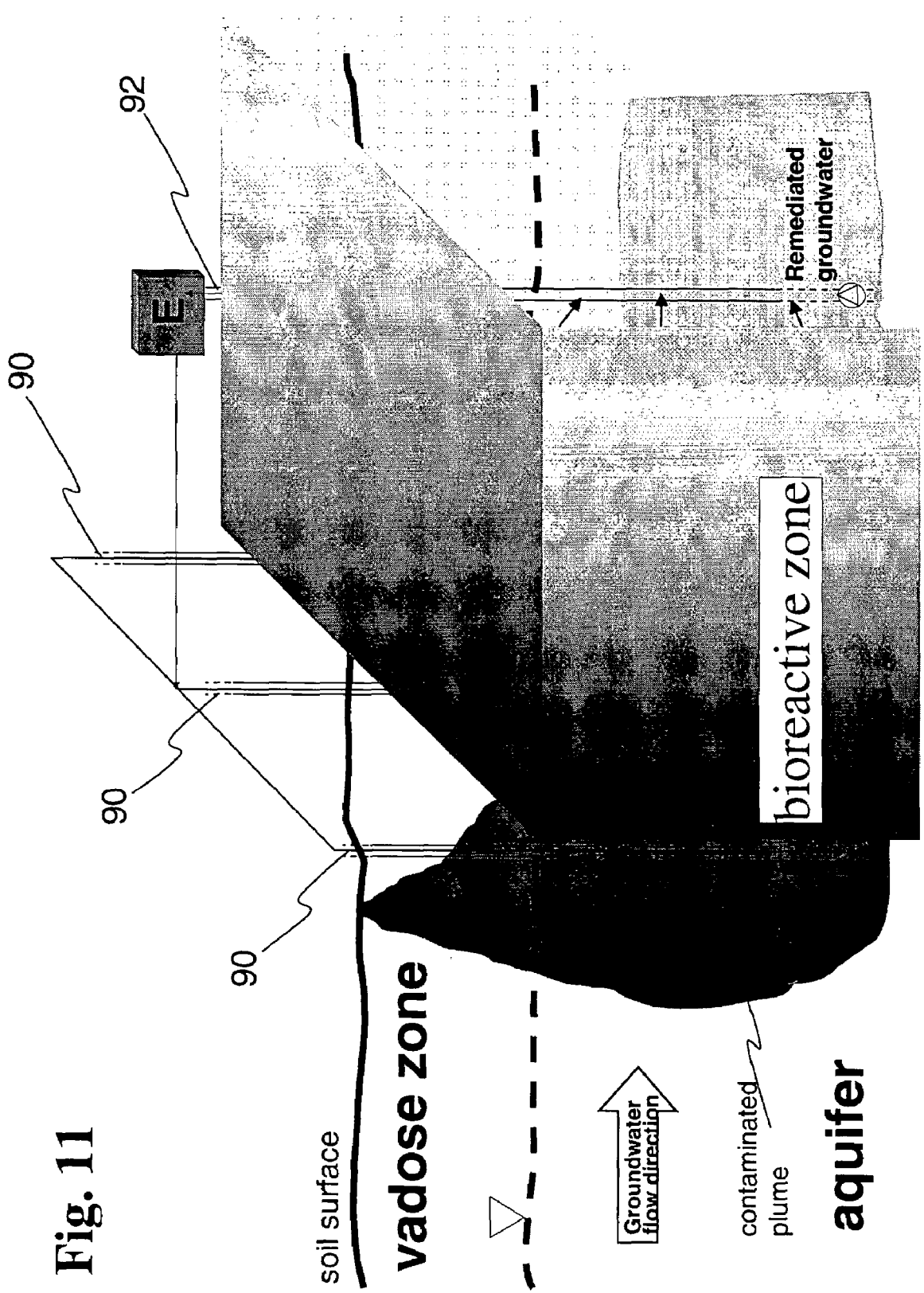

FIG. 11. Schematics of bioreactive zone, sustained within the aquifer portion between the injection and extraction wells' setup, according to the invention.

Figure 12:
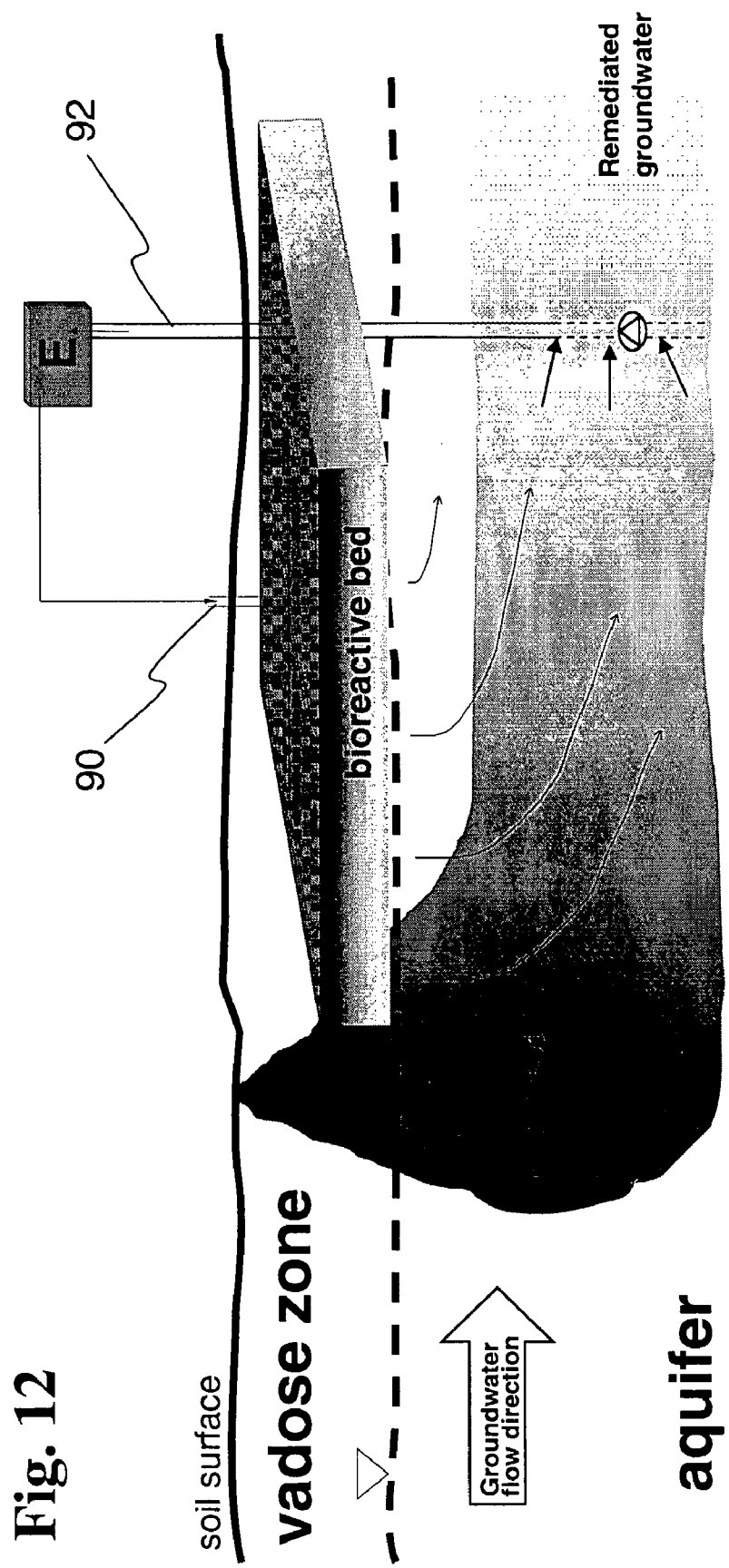

FIG. 12. Schematics of Biobed (downflow active process), according to the invention.

DETAILED DESCRIPTION OF THE INVENTION

Figure 4:
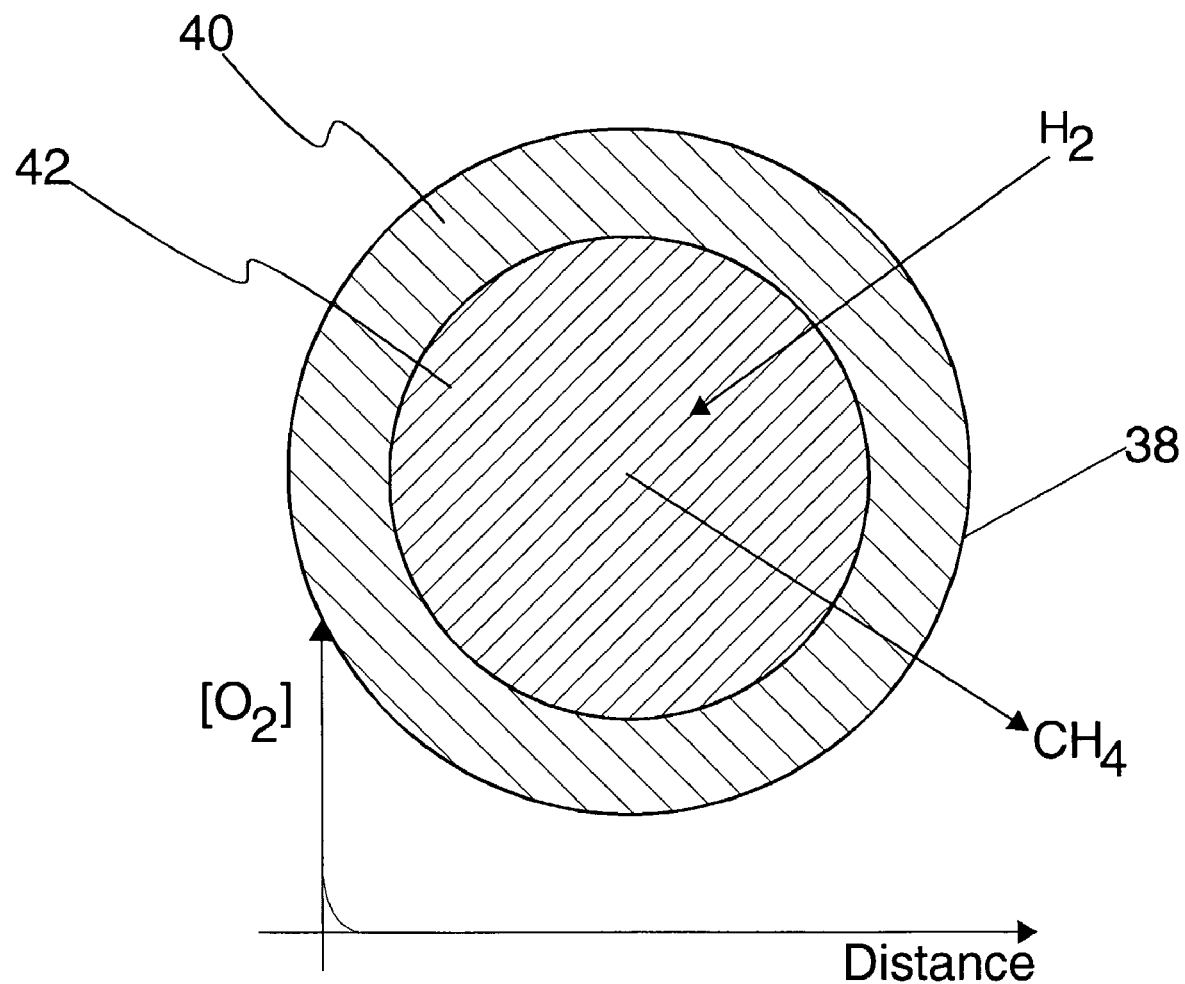
FIG. 4. Schematic of granular biofilm model for the single-stage methanogenic/methanotrophic coupling according to the invention FIG. 5. Graphic illustration efficacy of $^{14}C$-labeled TCE mineralization (i.e. % recovery as $^{14}CO_2$) under abiotic (●), heterotrophic aerobic (in presence of BES (bromo-ethane-sulfonate) which is a specific inhibitor of $CH_4$ production) (■) and methanotrophic ((( ) conditions (in presence of CH4 and O2 only).

According to the present invention, we propose a bioremediation method which couples activities of aerobic and anaerobic microorganisms for the biodegradation or mineralization of chlorinated organics, more specifically methanotrophic bacteria for the group of aerobic bacteria and methanogenic bacteria, for the group of anaerobic bacteria, by engineering methanogenic/methanotrophic biofilms (by methanotrophic selective enrichment of methanogenic nuclei, as seen in FIGS. 1a and 4, under accurate oxygenation control) and develop a single-stage bioprocess, capable of faster and more complete degradation of chlorinated contaminants (namely PCE, TCE, TCA, TCP), as compared to conventional systems. With respect to degradation of PCE and TCE, reductive conditions, provided by the methanogenic bacteria, allow for the first steps of transformation (dechlorination) which are non-specific and relatively fast. With respect to degradation of TCE and derivatives, methanotrophs are of prime importance as they possess the methane monooxygenase (MMO) enzyme. This enzyme catalyzes the first step in the methane metabolism of these bacteria, which is the oxidation of methane to methanol. The specificity of this enzyme is low and is capable of oxidizing compounds other than methane. In the case of TCE, MMO oxidizes TCE to form TCE epoxide and in the case of DCE, MMO oxidizes DCE to form DCE epoxide.

Conditions for the growth and activity of the methanotrophic bacteria have to be provided to exploit their ability to degrade TCE, DCE, etc. Specifically, methane as a carbon source and oxygen as an electron acceptor must be readily available to the methanotrophs. In the prior art, both gases were supplied by injection into the bulk liquid phase of the system. However, the transfer of gaseous methane into the aqueous liquid phase is difficult due to its low solubility therein. According to the invention, direct additions of oxygen and methane are avoided by providing methanogens in proximity to the methanotrophs, to produce methane in-situ, thus avoiding the problem of transfer of methane into the liquid phase. The needs of the methanogens must also be addressed. Methanogens are strict anaerobes, and have to survive while in the presence of oxygen in the bulk fluid.

The carbon source is also used by the facultative and aerobic heterotrophic bacteria in the outermost layer of the biofilm, to reduce part of the oxygen and shield the inner strict anaerobes from oxygen. But at the same time, those heterotrophic bacteria are fiercely competing with methanotrophic bacteria for oxygen, and doing so, limiting the methanotrophs proliferation at a lower level than expected, as mentioned earlier. To resolve such a limiting antagonism, we propose according to one aspect of the invention, to use water electrolysis to generate hydrogen and as such, to supply electron donors to methanogens and reductive dechlorinators.

Moreover, at the same time, a solution to the oxygen supply is also provided, since water electrolysis also generates oxygen (at half the volumetric rate of hydrogen) which is used as electron acceptors by aerobic bacteria (including methanotrophs)

It is not new to combine electrolysis of water with a biological system, but to our knowledge, up to now only one of the two gas species produced by electrolysis was utilized. In some instances of bioremediation, oxygenation was effected by electrolysis, but $O_2$ alone was used (Franz et al. 2002). In another case, it was $H_2$ that was generated by electrolysis for supplying electron donors to denitrifying bacteria, but the oxygen was discarded and at a cost (Felekea & Sakakibarab 2002). One novel aspect of this invention is that both gas species are useful in a single biofilm system. Hydrogen is used both by strict anaerobes to reductively dechlorinate chloroaliphatics into intermediates, and by methanogens to reduce water carbonates into $CH_4$; while oxygen is used by methanotrophs to oxidize $CH_4$, and to co-metabolically degrade the chlorinated intermediates. The immediate advantage of using electrolytic $H_2$ is not to depend on an organic carbon-source for the electron donors for both reductive dechlorination and methane production (providing the medium is carbonated enough). Yet a minimal supply of a carbon-source for facultatives and heterotrophs may be necessary to make sure $O_2$ diffusion is limited into the biofilm matrix and anaerobic niches preserved. However the required organic carbon flux is expected to be minimal which should diminish the competition between methanotrophs and heterotrophs for oxygen.

Figure 3:
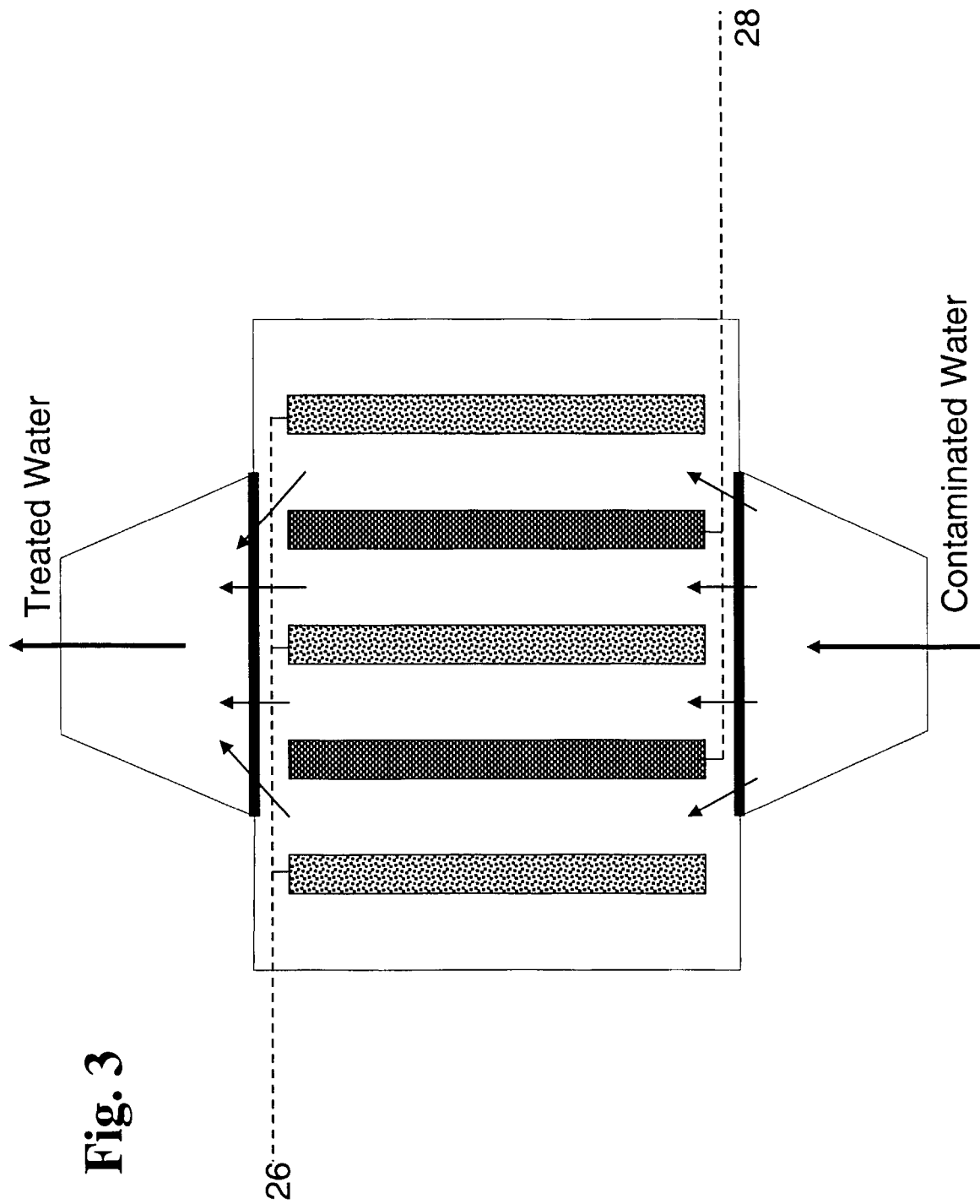
FIG. 3. Schematic side view of electrolytical cartridge according to the invention with multiple electrode sets (and surfaces).

According to the invention as seen in FIG. 1a the basic apparatus for continuous electrolytic methanogenic/methanotrophic coupled (eMAMOC) biotreatment of contaminated water comprises a bioreactor 10 of the upflow (expanded or static) bed-type, although it will be appreciated that other forms may also be employed. Waste liquid influent inlet means 12 is provided at the lower end of the reactor, and waste liquid effluent outlet means 14 is provided at the upper end of the reactor. Effluent by-product gas (methane, carbon dioxide etc.) outlet 16 is also provided at the top of the reactor. Conduit means 18 connects the inlet and outlet means to define a closed loop for circulating the waste liquid through the apparatus. De-contaminated effluent liquid is lapped off from the liquid outlet conduit means. Oxygenating means is associated with the circulating closed loop conduit. Water electrolysis within an electrolytic cell 20a is used for oxygen supply. At the same time hydrogen is also produced by the water electrolysis. Power is provided by a DC power supply. The electrolytic cartridge (or cell, or chamber) may be designed as illustrated in FIG. 2a. A set of two flat electrodes (one cathode 26, negative electrical charge, hydrogen generating, and one anode 28, positive, oxygen generating). The anode can be made of titanium coated with iridium-dioxide (DSA, dimensionally stable anode), and the cathode, of stainless steel 300-400, or graphite, although it will be appreciated that any other material suitable for electrode and stable electricity production may be employed. The anode and cathode are separated by a non-conductive porous or permeable separator 30, or by a liquid void volume used as a spacer. The electrolytic cell 20a is placed such as to be crossed upward by the system liquid recirculation flow; the cell inlet 32, placed at the cell bottom (or on one side), is thus connected at the pipe 18 coming from recirculation pump 34; the electrolytical chamber outlet 36, placed at the cell top (or on the other side), at the pipe going to the inlet 12 at the bottom of the bioreactor body. The circulating liquid flows through the electrolytic cell which is thus continuously enriched in both $H_2$ and $O_2$. The liquid flow rate is set such as to be sufficient to wash out the microbubbles generated at the surface of the electrodes. A thin and rectangular shape of the electrode chamber is preferred as it will maximize the liquid linear velocity in the chamber. Other shapes are also possible, as well as multiplication of the electrode sets (and surfaces), depending on the current intensity which is needed at a given voltage (FIG. 3). The liquid might also travel transversally from one side to the opposite side, depending on the cartridge shape and the electrode arrangement. The length of the liquid conduit from the electrolytic chamber outlet 34 to the bottom of the bioreactor body and gas inlet 12 is fixed such as to optimize the gas species transfer from the bubbles to the liquid phase (dissolution): in such an arrangement, gas transfer might be readily above 50%. The amount of oxygen dissolved is controlled by conventional means (not shown), so that the amount of dissolved oxygen is kept below the rate of consumption by the bioreactor. It is noteworthy that the electrolytic cell is a closed vessel, and thus the stripping by the gas production at the electrodes does not result in loss of volatile compounds.

A coupled anaerobic/aerobic biofilm means 38 is suspended in the bioreactor between the inlet and outlet means. As best seen in FIG. 4, the biofilm 38 (of about between 1 and 3 mm of diameter or thickness) includes an outer surface area 40 (of maximum 200 μm of thickness) and an inner core area 42, and has a decreasing gradient of oxygen concentration toward the core area (see graph portion of FIG. 4) which is substantially oxygen-free. Predominantly, strict aerobic bacteria including methanotrophs are located at the outer surface area. Predominantly, strict anaerobic bacteria including methanogens are located at the core area. The core area may include inert microcarrier granules (ie. of a particle size of between 300 and 600 μm, that have a highly porous structure and high specific surface area, such as: perlite, puzzolane, pumice, Biolite®™ (or Argex™, or any other expanded clay particles), vermiculite, diatomite, sepiolite, sintered glass, granulated activated carbon, styrene beads, reticulated polyurethane beads, peat moss, or any other suitable porous microparticle) which could nucleate the cell immobilization and stabilize the suspended biofilm. The biofilm could also be made of a fixed biofilm system, packed with fixed inert support to develop a fixed methanogenic/methanotrophic biofilm. Pump means 34 is associated with the conduit means to cycle the waste liquid through the electrolytic cell.

According to another aspect of the invention, a method for the continuous methanogenic/methanotrophic coupled single-stage biotreatment of contaminated water is provided, comprising (a) providing a biosystem containing a coupled single-stage anaerobic (including methanogenic)/aerobic (including methanotrophic) biofilm;

(b) cycling the liquid to be treated outside of said biosystem, within an electrolytic device to produce $H_2$ and $O_2$ and to a introduce a controlled amount of dissolved oxygen and hydrogen into the said circulating liquid and (c) continuously cycling the oxygenated and hydrogenated liquid through said biosystem to remove said contaminants, by feeding with $O_2$ and $H_2$ as electron acceptor and donor respectively, wherein the biofilm comprising an outer surface area containing predominantly aerobic bacteria and an inner core area containing predominantly anaerobic bacteria, provides a decreasing gradient of oxygen concentration toward said core area, the core area being substantially oxygen-free, while hydrogen, not reacting in the aerobic environment of the periphery, can readily reach the said core, and effectively act as an electron donor.

The rate of oxygen consumption by the biofilm is fixed (because limited) by the oxygen supply rate and the efficiency of transfer from the gas to the liquid phases. The oxygen supply rate is a function of the power applied to and the surface area of the electrodes. The oxygen transfer efficiency is a function of the liquid retention time within the recirculation line ie. the liquid recirculation rate through the apparatus (high ratio of effluent recirculation to influent flow), and the liquid turbulence.

Thus, a system is formed of biological components in synergism (mutualism) at two levels:

at the level of the electron donors: the $H_2$ will serve as electron donor for reductive dechlorination and for production of $CH_4$ by methanogenic bacteria, which will be then used as energy and carbon-source by methanotrophic bacteria;

at the level of the degradation of the chlorinated compounds: first step of degradation (reductive dechlorination) by methanogens complemented by the methanotrophic mineralization.

As another embodiment of the invention, we propose an alternative scheme for implementing the bioelectrolytic methanogenic/methanotrophic coupling, considering a different bioreactor configuration. Coupling is provided by a methanogenic zone 22 in a lower part of the biosystem, and a methanotrophic zone 24, in the upper part of the system, i.e. a dual system is used. As the methanotrophic zone superimposes the methanogenic zone and because of the fluid continuity between the two zones, the methane produced in the methanogenic zone is allowed to rise and freely pass to and feed the methanotrophic zone (FIG. 1*b*). Simultaneously, compounds partially dechlorinated in the methanogenic zone 22 are transported to the methanotrophic zone 24. For such a dual zone system to be operable, the $H_2$ and $O_2$ fluxes are dissociated. This is done by duplicating the liquid recirculation lines 37, 37*a* out of the electrolytic cell. This means the electrolytic cell 20*b* contains two parallel chambers, one with the cathode 26, the other with the anode 28. A porous separator 30, permeable to liquid and electrolytes, is installed in the middle (FIG. 2*b*). In that case, the recirculation pumps 34 are also duplicated and placed after the electrolytic cell, pulling the liquid out of the cell chambers. The design principles are the same as for the one-chamber cell. The high liquid linear velocity will drive the $H_2$ and $O_2$ microbubbles out the chambers respectively in the separate conduits 37, 37*a* such that $O_2$ is provided to the methanotropic zone 24 and $H_2$ to the methanogenic zone 22 via inlets 13 and 12 respectively, before they may migrate through the porous wall and mix. Within such a design, $O_2$ will mix with $CH_4$ only in the upper part of the biosystem, making it an area essentially methanotrophic, since the main carbon-source there would be $CH_4$. Thus the competition of heterotrophs and methanotrophs for oxygen is virtually eliminated. Also, in the bottom part 22, no exogenous carbon-source (other than $CO_2$) is necessary, since the electrolytic $H_2$ acts as the electron donors (for $CH_4$ generation and chloroorganics reductive dechlorination). In such a design, the methanogenic and methanotrophic populations are spatially distant, which is a shortage as compared to the close synergism between the two populations that we have in the single-stage system, which reduces the diffusion paths and avoids toxicity of intermediates. Yet this might be a more straightforward way for giving a selective advantage to the methanotrophs. And although the methanogenic and methanotrophic populations are spatially distant as said, the system still keeps some integration characteristics as there is a relatively high turnover (recirculation) of liquid.

Furthermore even though anaerobic populations would not be that critical for the degradation first steps i.e. that methanotrophic degradation of the primary molecules would not be that limited, methanogenic populations in the coupled system yet are of utility as an effective source of indigenous $CH_4$ i.e.

the anaerobic nuclei in the single stage embodiment or the anaerobic compartment in the dual-stage embodiment can be viewed as an intrinsic or in situ methane releasing component, avoiding the burden of methane injection or supply from an extraneous source, with limited transfer efficacy and additional cost.

Such a system has the potential for long-term and continuous operation with minimum energy or labour input.

Preliminary Results

Figure 5:
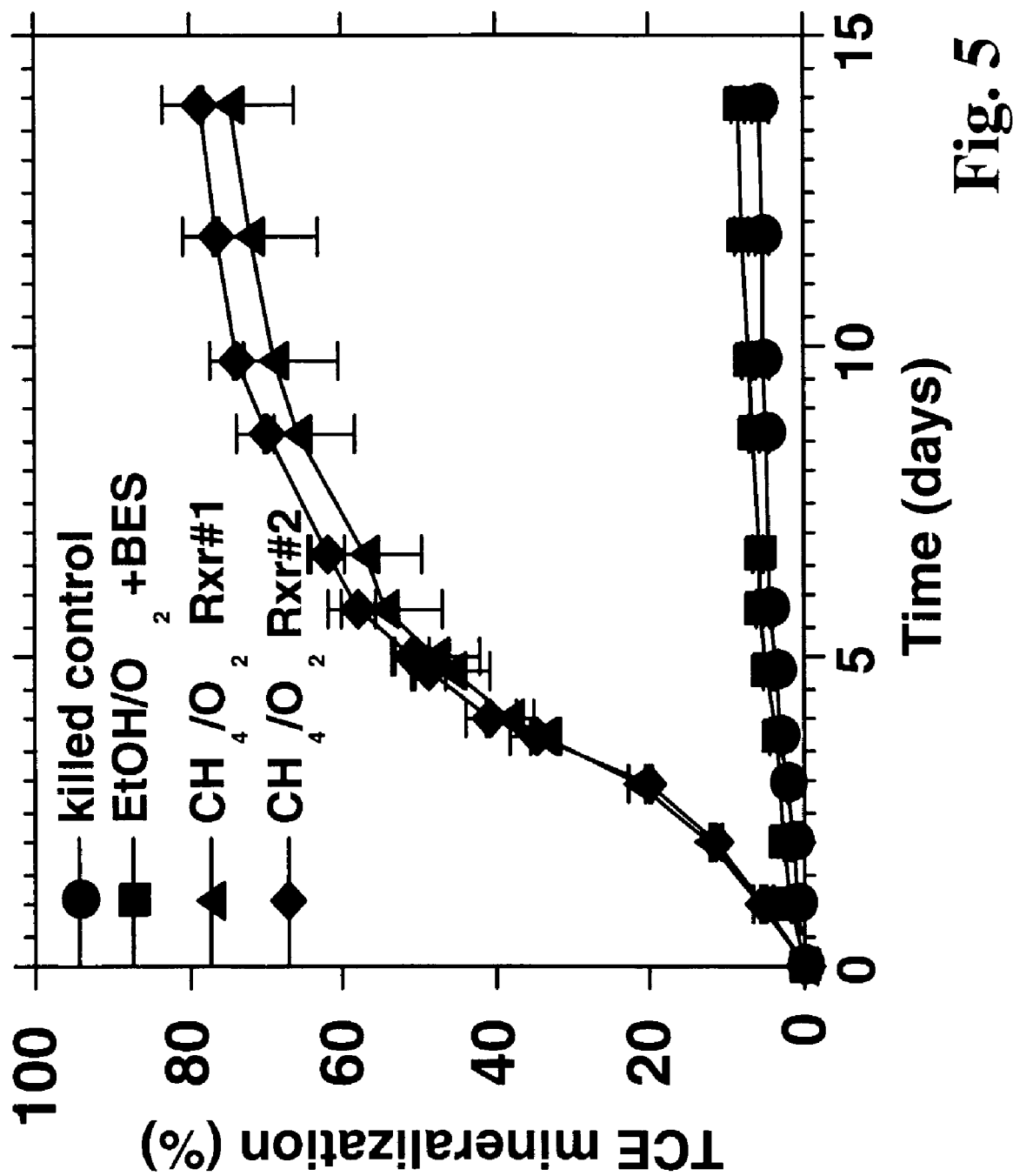

Superiority of the methanogenic/methanotrophic coupled system over either aerobic or anaerobic process alone, or sequential systems, as coupling minimizes diffusion pathways and eliminates toxic intermediates. Assays with $^{14}$C-labeled TCE showed that the methanotropic activity induced in the coupled system was central in the completeness of the reactions (FIG. 5). The TCE complete dechlorination specific rates from methanogenic/methanotrophic reactors is in a range of one order of magnitude larger than the mineralization specific rates under methanotrophic conditions alone. It is hypothesized the methantroph-induced mineralization of TCE is more limited than the aggregate of initial reductive dechlorination steps (fast) and methanotrophic mineralization of less chlorinated intermediates (assumed as fast also).

Preliminary Evaluation as a Single-Stage System.

A preliminary evaluation of the electrolytic methanogenic/methanotrophic coupled (eMaMoC) system for PCE treatment was carried out at the lab-scale in single-stage reactors inoculated with unadapted anaerobic sludge granules.

Setup and operational conditions. The 5-L glass-made reactors (internal diameter, 10 cm) were operated in an upflow sludge bed (USB) mode with an effluent liquid recirculation flow rate such as to maintain the in-reactor liquid upflow velocity between 0.4 and 2 m/h. The reactor influent was introduced to the effluent recycling line in four sidestreams of dilution water (buffer), nutrient solution, trace metal solution, and PCE solution. The dilution water consisted of (mg/L): $NaHCO_3$, 760; $KHCO_3$, 990; $Ca(NO_3)_2.4H_2O$, 27; $K_2HPO_4$, 2840. The nutrient solution contained (mg/L): $KH_2PO_4$, 880; $K_2HPO_4$, 1030; $NH_4HCO_3$, 12450. The chloride-free trace metal solution contained (mg/L): $FeSO_4.7H_2O$, 856; $H_3BO_3$, 5; $ZnSO_4.7H_2O$, 13; $MnSO_4.H_2O$, 60; $Co(NO_3)_2.6H_2O$, 33; $NiSO_4.6H_2O$, 9; $(NH_4)_6Mo_7O_{24}.4H_2O$, 273; $AlK(SO_4)_2.12H_2O$, 2; $Na_2$-EDTA, 33; $MgSO_4.7H_2O$ 1630; $Na_2SeO_4$, 2; $Na_2WO_4.2H_2O$, 6; cystein, 320. The PCE solution was prepared in an SKC Quality sample bags (tedlar, SKC Inc, Eighty-Four, Pa.) at a concentration of 22-70 mg/L of PCE. Ethanol, which facilitated the dissolution of PCE, was adjusted so as to have an organic load of 250 mg chemical oxygen demand (COD)/liter of reactor ($L_{rx}$)·d. The dilution water: trace metal solution:nutrient solution ratio in the feed was 375:1:1 (vol./vol.).

The electrolytic cell, which was crossed upward by the liquid recirculation flow, was continuously enriching the reactor liquid in both $H_2$ and $O_2$. The electrodes (5 cm×10 cm) were made of titanium coated with iridium-dioxide (Magneto, Schiedam, Netherlands). The applied electrical power varied from 0.8 to 1.1 W: this generated oxygen at a rate varying between 240 and 440 mg $O_2/L_{rx}$·d, 20-70% of which were estimated to be transferred into the aqueous phase. Abiotic tests were carried out showing a maximum dechlorination of 5% by the electrolysis alone.

The COD (Standard methods, APHA 1995), pH (model PHB-51, Omega, Stamford, Conn.), inorganic chloride ($Cl^-$) were monitored in the effluent throughout the experiment. PCE and other chlorinated compounds were analyzed both in solution and in the off gas. Dissolved $O_2$ (DO) was controlled both in the inlet and effluent liquid (polarographic probe, Cole Palmer Instruments, Chicago, Ill.). Dissolved $CH_4$ was measured by adding 1.5 mL of liquid sample to 2 mL glass vials. The vials were sealed and vortexed for 5 min. A 300 μL sample of the headspace gas of the vials was taken and injected into a gas chromatograph (GC). The Henry's constant was used to calculate the $CH_4$ content in the liquid phase of the vial from the $CH_4$ percentage in the vial headspace. The two values were then summed and reported to the vial liquid volume for estimating the dissolved $CH_4$ concentration in the liquid.

The first reactor was operated for 6 months at a hydraulic retention time (HRT) of 1 day and at a temperature of 25° C. A second reactor was operated for a 4 month period, at an average HRT of 6.3 days and a temperature of 22° C. The electrical power applied was 0.4±0.2 W; oxygen was generated at a flow rate of 39 to 45 mg $O_2/L_{rx}$·d, 95% of which were estimated to be transferred into the aqueous phase. The ethanol load was decreased at 50 mg $COD/L_{rx}$·d.

Analytical Methods.

The inorganic chloride content of the influent and effluent was determined using a high-performance liquid chromatograph (HPLC, pump model 600, autosampler model 717 plus) equipped with a Dionex IonPac AS15 column (250×2 mm) and a conductivity detector (Waters Millipore, Milford, Mass.). Liquid analysis of PCE and chlorinated metabolites was done by adding 10 mL of sample to 20 mL glass headspace vials. The vials were sealed and heated for 60 min in an 80° C. water bath, and a 300 μL sample of the headspace of the bottles was taken and injected into an Agilent Technologies 6890N Network GC System System with a flame ionization detector (FID) (Hewlett-Packard, Wilmington, Del.) equipped with a 1.8 m Carbopack B/1% SP-1000 column (Supelco, Bellafonte, Pa.) and using helium as the carrier gas. The oven temperature was programmed at 50° C. for 1.25 min, 60° C./min to 220° C. which was maintained for 6 min. The concentrations of chloroethenes were calculated using standards curves constructed by GC analyses of solutions with known concentrations of each compound to be analyzed. The reactor gas content in chloroethenes and ethene was analyzed directly by injection of 300 μL of the reactor off gas into the GC as above. The concentrations were calculated using standards curves obtained with calibration gas mixes with known concentrations of each volatile compound, from Liquid carbonic (Praxair, Danbury, Conn.) and Scott Specialty Gases (Plumsteadville, Pa.). The reactor gas composition ($O_2$, $H_2$, $CH_4$, $N_2$) was measured by injecting 300 μL of the reactor off gas into a HP 6890 Series GC System (Hewlett-Packard, Wilmington, Del.) equipped with a FID and a 11 m×3.2 mm 60/80 mesh Chromosorb 102 column (Supelco, Bellafonte, Pa.) and using argon as the carrier gas. For analyses of methane and hydrogen, the column temperature was held at 50° C. for 3.9 min isocratic. For analyses of oxygen and nitrogen, the column temperature was held at 35° C. for 7.5 min, then programmed to 100° C. at a rate of 75° C./min, and finally held at 100° C. for 6 min. A 0.5 µL sample fortified 1:1 with internal standard (isobutyric acid) in 6% formic acid was directly injected onto a 1 m×2 mm glass column containing Carbopack C (60-80 mesh) coated with 0.3% Carbowax 20M and 0.1% H3PO4. Ethanol measurement was made on a Hewlett Packard 6890 GC coupled to a FID. A 1 µL liquid sample was injected onto a 2 m×0.03 mm Hayesep Q micropacked column from Supelco. The column is heated at 60° C. one minute then raised to 240° C. at a rate of 20° C./min. Helium is used as carrier gas.

Results. Under anaerobic conditions (DO=0), PCE was transformed into DCE which accumulated in the bioreator, while under anaerobic/aerobic conditions, over 50% of the cis-DCE was mineralized (Table 1).

TABLE 1

PCE degradation results of two single-stage 5-L eMaMoC reactors.

| Dissolved $O_2$ (DO) mg/L | $v_{UP}$ m/h | PCE in mg/L | PCE removed µM | % [1] | 1,2-cis-DCE out % [1] | Mineralization [3] % |
|---|---|---|---|---|---|---|
| \multicolumn{7}{c}{Reactor I: HRT 1 d} |
| 0 | 2 | 6.1 | 37 | 94 | 92 | 2 |
| 0.6-3 | 1 | 7.4 | 45 | 95 | 76 | 16 ± 4 |
| 3-4 | 1 | 5.6 | 34 | 98 | 46 | 48 ± 4 |
| 5-8 | 1 | 4.3 | 26 | 98 | 48 | 53 ± 7 |
| \multicolumn{7}{c}{Reactor II: HRT 6.3 d} |
| 1.5 | 0.43 | 8.6 | 52 | 98.1 [2] | 65 [2] | 31 ± 17 |
| 2.3 | 0.75 | 8.6 | 52 | 99.5 [2] | 40 [2] | 58 ± 8 |
| 2.2 | 0.75 | 5.5 | 33 | 98.5 [2] | 14 [2] | 83 ± 5 |

$v_{UP}$ liquid upflow velocity in reactor
[1] includes off gas loss: PCE <2%; DCE <4%
[2] includes off gas loss: PCE 0.1%; DCE 0.02%
[3] based on mole balance between the inlet PCE and all products in the outlets (off gas and liquid)

Although the extent of PCE dechlorination and mineralization augmented as the conditions became more oxidative (indicated by DO increase at the inlet, resulting from a power increase in the electrolytic cell), DCE mineralization seemed to be intrinsically limited at a level of less than 60% for an HRT of 1 d. With an HRT of 6.3 days, a higher DCE mineralization efficiency could be obtained (Table 1), however, the maximum mineralization efficiency that could be reached was only 83%. Mineralization results were corroborated by the stoichiometric recovery of inorganic chlorine in the effluent. The mineralization efficiency limit was probably related to the DCE oxidative degradation kinetics and/or the DCE-oxidizing microorganisms content in the granular biofilm and the liquid medium.

Kinetics Study of the eMaMoC System in the Dual-Stage Mode.

Experimental Setup.

For the sake of elucidating the functionality of the coupled biosystem, a 5-L glass-made reactor was set up as a two-stage assembly aimed at segregating methanogens and methanotrophs within the bottom and upper parts of the reactor, respectively. See FIG. 1b.

The bottom methanogenic zone 22 was inoculated with unadapted industrial anaerobic granules, while the upper methanotrophic zone 24 was packed with a porous support made of granulated perlite silicate, and inoculated with activated sludge. Accordingly the liquid recirculation was bifurcated out of a two-chamber electrolytic cell 20b: a line 37 from the cathodic chamber carried $H_2$-enriched liquid to the bottom inlet 12 of the reactor 12, and a line 37a from the anodic chamber, delivered $O_2$-enriched liquid to the middle inlet 13 of the reactor. Because of the fluid continuity between the two reactor stages, $CH_4$ produced in the lower stage rises and feeds the methanotrophic upper compartment, together with compounds partially dechlorinated.

TABLE 2

Performance of the dual-stage eMaMoC reactor, under various operational conditions, for an operational period of 17 months.

| HRT D | PCE load mg/L$_{rx}$·d | PCE$_{in}$ µM | PCE degrad. % [1] | DCE$_{out}$ % [1] | Mineralization % [3] | $X_{rx}^{aer}$ g VSS/L$_{rx}$ | $k_{max}^{DCE}$ µmol/gVSS·d |
|---|---|---|---|---|---|---|---|
| 1 | 6.2 ± 1.3 | 34 ± 6.6 | 98 ± 0.1 | 49 ± 3 | 49 ± 5 | ~0.8 | n.d. |
| 4 | 0.9 ± 0.2 | 22 ± 5 | 95 ± 3 | 34 ± 10 | 62 ± 10 | ~0.9 | 1.15 |
| 8 | 1.1 ± 0.2 | 50 ± 6 | 97 ± 3 | 32 ± 4 | 64 ± 4 | n.d. | 2.3 |
| 24 | 0.35 ± 0.04 | 46 ± 9 | 100 ± 0 | 15 ± 5 | 85 ± 5 | 1.4 | 3.9 |
| 47 | 0.24 ± 0.09 | 59 ± 19 | 100 ± 0 [2] | 5 ± 6 [2] | 95 ± 5 | ~0.7 | n.d. |

$X_{rx}^{aer}$: biomass content in the aerobic upper compartment, reported to the overall reactor volume
$k_{max}^{DCE}$: maximum specific DCE mineralization rate
[1] includes off gas losses: PCE <1%; DCE <1%
[2] PCE, DCE not detected in off gas
[3] based on mole balance between the inlet PCE and all products in the outlets (off gas and liquid)
VSS: volatile suspended solids
n.d.: not determined Results and Discussion.

The system was operated at a PCE inlet concentration which varied from 13 to 60 µM, a PCE load, from 37 to 1.5 µmol/L$_{rx}$·d, and an HRT, from 1 to 47 days, for 17 months. PCE dechlorination to DCE in the first stage was always between 95 and 100% while in the second stage, DCE mineralization improved from 49 to near 100% with the HRT increase (Table 2). During the last steady state, no chlorinated ethenes were detected in the reactor gas phase, while in the liquid phase, average concentrations (ppb, standard deviation in brackets) for PCE, TCE, 1,2-cis-DCE and vinyl chloride (VC) were as following: 31 (38), 0, 168 (124) and 3 (8), respectively. The aerobic biomass colonization of perlite slightly increased, at least till the 12$^{th}$ month of operation (end of the period at an HRT of 24 d), while its methanotrophic DCE-oxidizing potential achieved a three-fold increase.

Eight months after the startup of the dual-stage system, kinetics parameters ($K_S$ and $k_{max}$) of the upper methanotrophic biomass were estimated for DCE mineralization under strict methanotrophic conditions. Mineralization of DCE was assayed for a range of initial DCE concentrations, in 120 ml serum bottles equipped with a KOH trap and spiked with $^{14}$C-uniformly-labeled DCE (80,000 dpm), as described elsewhere (Lyew et al. 2002). Abiotic controls were obtained by autoclaving the biomass (30 min at 121° C., 3 times). The radiolabeled $CO_2$ trapped in the KOH solution was quantified periodically using a scintillation counter (model 2100 TR, Packard Instrument Company, Meriden, Conn.). For each DCE concentration tested, the initial mineralization slope was reported to the biomass-VSS content in the assay to obtain the specific mineralization rate, $k_o$. Experimental values of $k_o$ and initial DCE aqueous concentrations ($C_o$) were fit into the Michaelis model ($k_o = k_{max} \cdot C_o / [K_S + C_o]$), using non-linear regression techniques. Values of 5 µM DCE and 1.15 µmol DCE/gVSS·d were obtained for $K_S$ and $k_{max}$, respectively. A substrate balance around the reactor at steady state ($C_e = C_o - k \cdot X_{rx}^{aer} \cdot HRT$) gives the residual substrate concentration in the effluent, $C_e$, as a function of the substrate inlet concentration, $C_0$, the biomass content, $X_{rx}^{aer}$, the in-reactor specific degradation rate, k, and the HRT. The latter equation and the Michaelis one can be simultaneously solved for expressing $C_e$ as a function of HRT and $C_o$, knowing $k_{max}$, $K_S$ and $X_{rx}^{aer}$, as following:

$$E(\%) = 100 \left( 1 - \frac{C_o - K_S - k_{max} \cdot X_{rx} \cdot HRT + \sqrt{(C_o - K_S - k_{max} \cdot X_{rx} \cdot HRT)^2 + 4 \cdot K_S \cdot C_o}}{(2 \cdot C_o)} \right)$$

This equation, plugged with the above kinetics parameters (i.e. 5 µM DCE and 1.15 µmol DCE/gVSS·d for $K_S$ and $k_{max}$, respectively), predicted that for an inlet PCE concentration of 50 µM and assuming all PCE was stoichiometrically reduced into DCE, an HRT of 14, 20 and 41 days would be necessary for the mineralization efficiency to exceed 70%, with an aerobic biomass content of 3, 2 and 1 g VSS/L$_{rx}$, respectively. Similarly, for the residual DCE concentration to be below 50 ppb, an HRT of 26 days would be required with an inlet PCE concentration of 1 mg/L and an aerobic biomass content of 2 g VSS/L$_{rx}$. This seems to indicate that the kinetics properties of the methanotrophic stage are instrumental in fixing the performance limit of the overall mineralization process. This likely explains in part the change in the mineralization efficiency from 49 up to over 83, then over 95%, when HRT was increased from 1 to 24, then 47 days (Table 2), although those results are significantly higher than those predicted as above for such actual conditions. Such discrepancy is likely explained by the presence of monooxygenase-possessing aerobes other than methanotrophs and their contribution to the DCE degradation. This anticipates DCE degradation standards are within reach providing both the aerobic biomass density ($X_{rx}^{aer}$) and its methanotrophic DCE-oxidizing potential ($k_{max}^{DCE}$) are optimized and HRT, accordingly adjusted.

In another experiment, in a set of two soil columns, designed to mimic both a bioreactive system and the adjacent aquifer, preliminary results with PCE are shown in the following Table 3. The bioreactive soil column had a volume of 6 L, packed with peat moss, inoculated with anaerobic sludge and methanotrophic enrichment, and operated with a HRT of 1 day. The electrical power applied to the electrolysis cell was 1.2-1.5 watts, resulting in a transfer of 50 to 120 mg $O_2$ per liter of column and per day.

TABLE 3

| Dissolved $O_2$ (DO) mg/L | PCE in mg/L | PCE removed % | 1,2-DCE out mg/L (%) | Dechlorination % | Mineralization % |
| --- | --- | --- | --- | --- | --- |
| 2-3 | 1.49 | 97 | 0.34 (39) | 71 | 61 |
| 2-3 | 0.98 | 100 | 0.04 (7) | 97 | 93 |

The results indicate that a single-stage bioelectrolytic coupled system can achieve a PCE mineralization almost complete, providing a certain PCE load is not exceeded, in this case 1 mg PCE/L$_{brx}$·day.

Applications

The above concept is easily implemented in a bioreactor system (FIG. 1a) (e.g. for wastewater anaerobic/aerobic biotreatment or, for ex situ bioremediation of a contaminated aquifer (ie. above-ground treatment of contaminated groundwater, using the so-called pump and treat approach).

When in situ (underground) remediation is preferred, the above concept is also easily implementable in a permeable reactive barrier (abbreviated as PRB) application (FIG. 6) taken in a broad sense. Indeed, in situ remediation of groundwater is most often preferred over ex situ groundwater treatment. And groundwater remediation by PRB is now established as one of the most cost-effective techniques. In the present applications, the reactive element is biological in essence, and abbreviated as PbRB, or biobarrier, taken as well in a broad sense, as detailed in the following paragraphs.

Figure 6B:
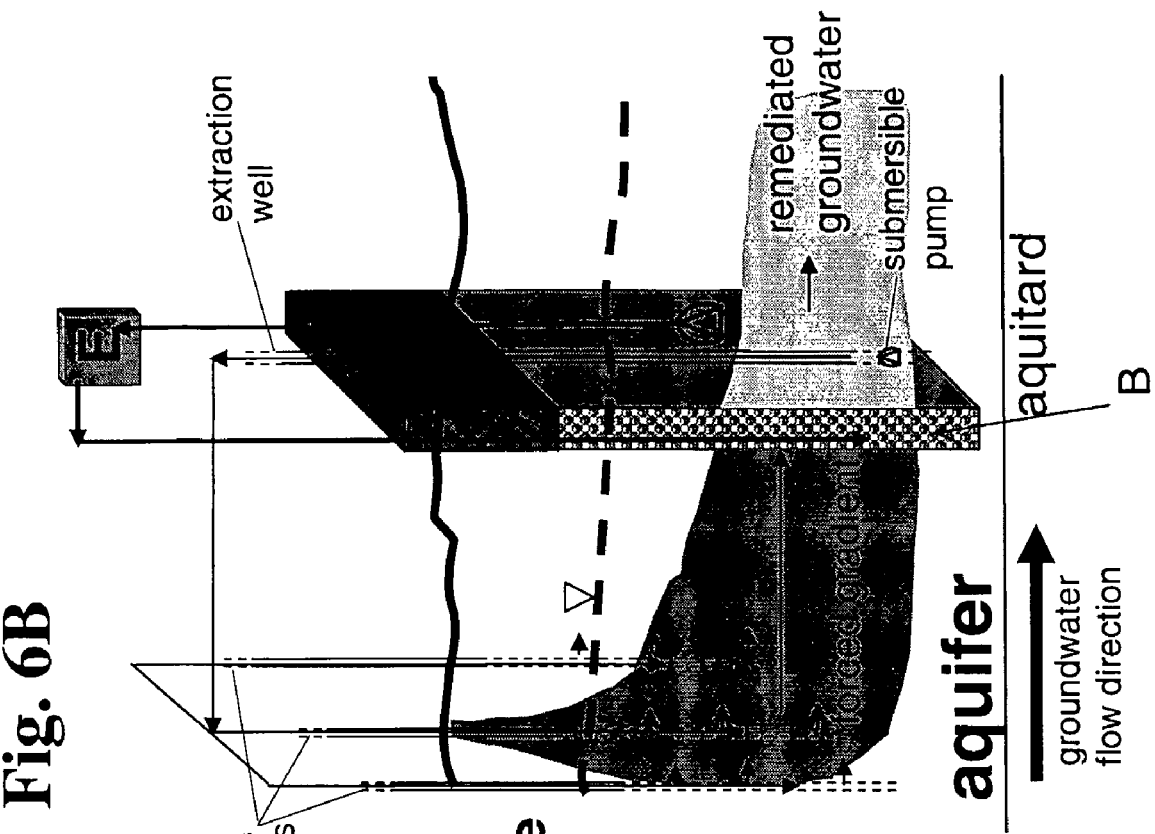
FIG. 6. Schematic view of the biobarrier, semi-active (a) versus active mode (b) according to the invention.
Figure 6A:
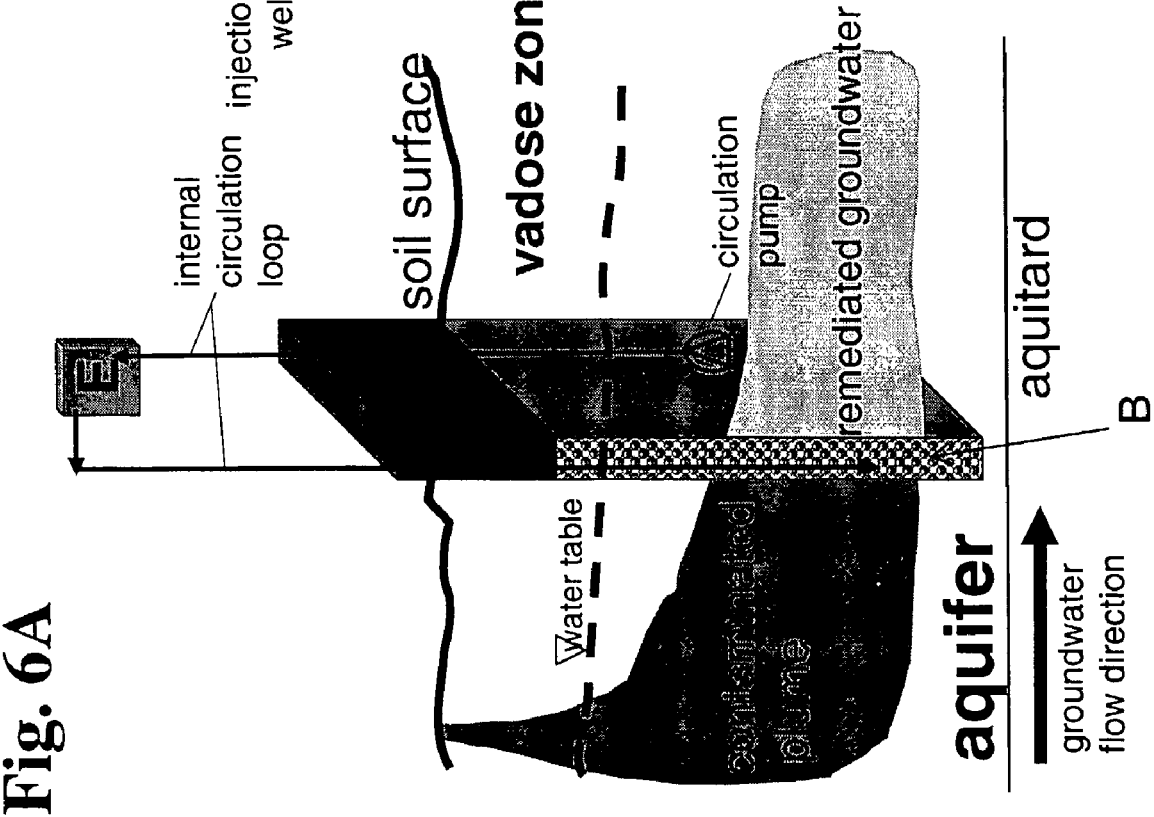

As seen in FIG. 6 the biobarrier comprises a permeable bioreactive zone, system or wall B placed in situ across the path of a contaminated plume. As the contaminated groundwater moves under natural (semi-active mode) or forced (active mode) hydraulic gradient through the permeable bioreactive component, the contaminants are removed or biodegraded. Decontaminated groundwater emerges from the downgradient side, thus preventing off-site migration of the dissolved-phase contamination, while not confining the groundwater. This mode of operation, which is the most commonly used, is typically called semi-active, as the groundwater flows through the bioreactive element as a function of the natural hydraulic gradient, as opposed to the active mode, where the groundwater passage through the bioreactive component is accelerated by the means of an extraction-injection setup. This may be used to clean contamination at the source, or to process decontamination at a depth that cannot be reached by a trench (in the case of a permeable wall), or by sheet pilings (in the case of a funnel and gate or a panel and drain). This active mode of treatment is typically used for sandy aquifers (i.e. coarse sand) with a sufficiently high hydraulic conductivity. The two modes are compared in FIGS. 6a and 6b, for the same bioreactive element. In the active mode, continuous pumping of water internally to the biological element, may also be required to supply at an independent rate sufficient amounts of $O_2$ and $H_2$ (electron acceptors and donors) through the electrolysis cell as well as nutrients and organic matter (source of carbon).

Figure 7B:
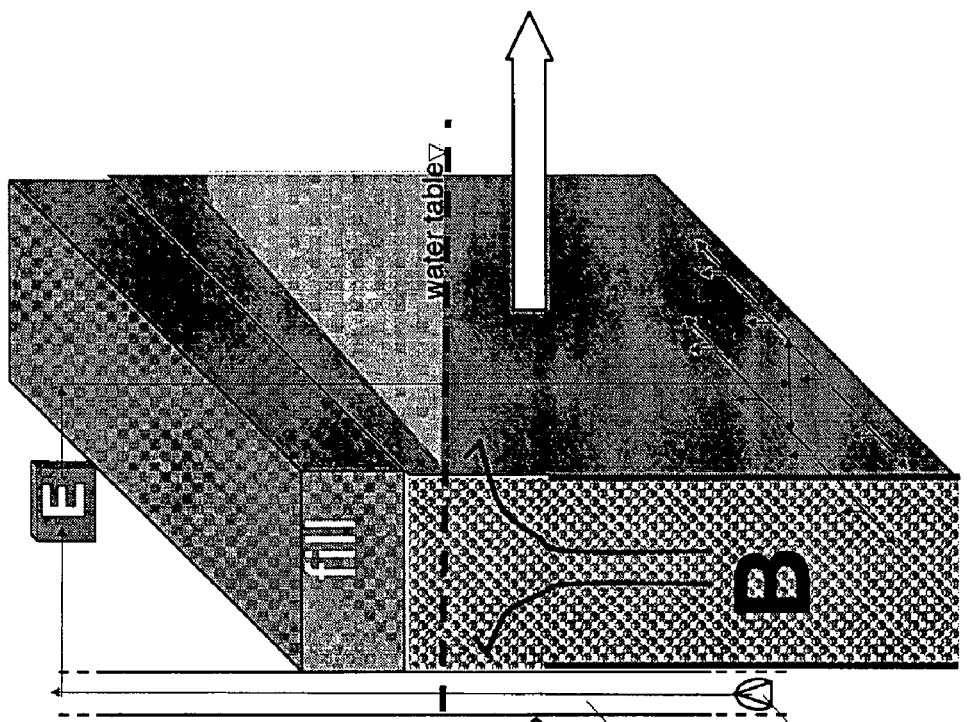
FIG. 7. Schematics of biobarrier, biotreatment wall, semi-active, detail of the internal circulation loop system; (a) conventional liquid recycling; (b) extraction in front of the biobarrier, such as to maximize the hydraulic gradient between the upstream sol and the biobarrier, and the ground water capture efficacy of the funnel, according to the invention.
Figure 7A:
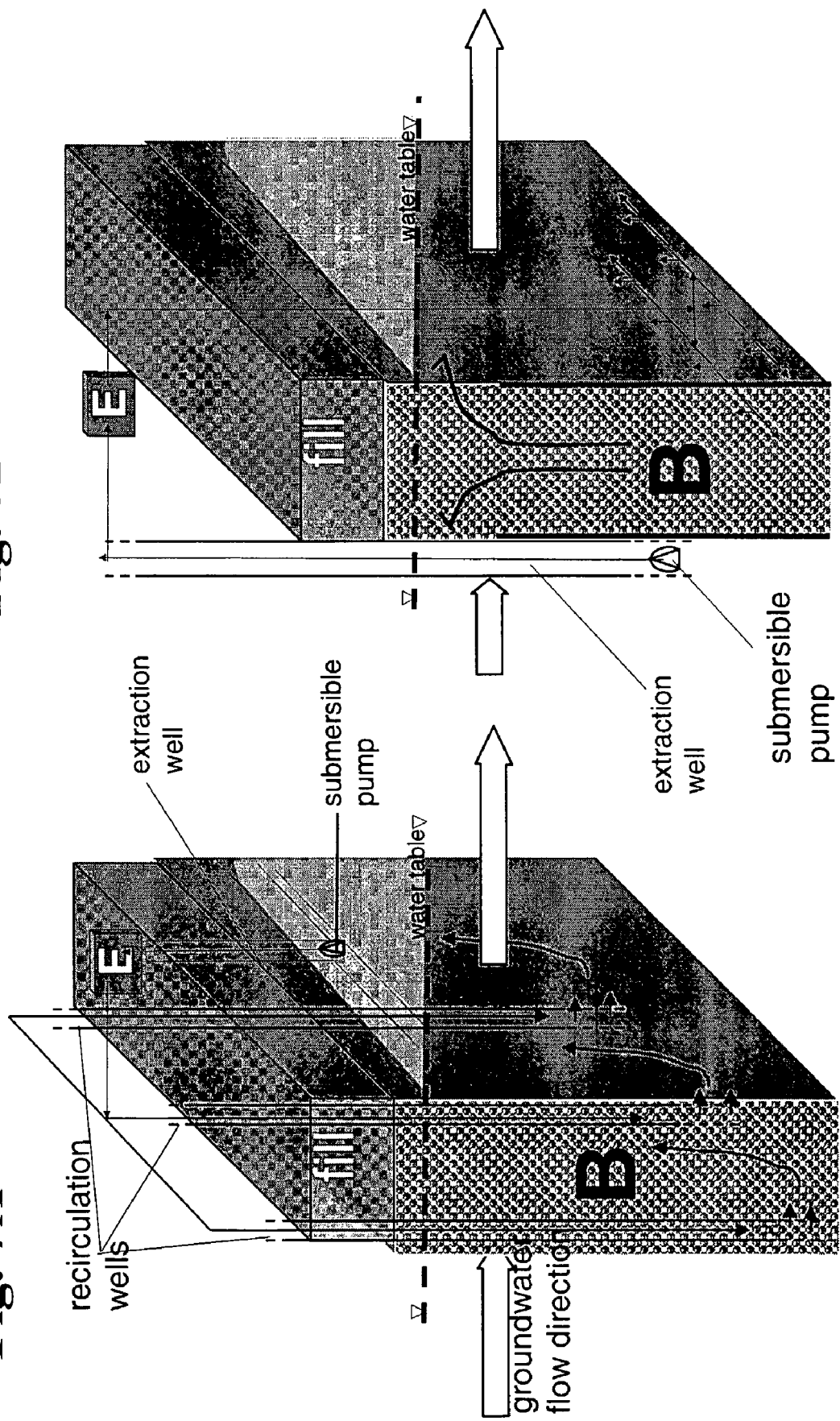

In one application, within the so-called semi-active category, the bioreactive component—apparatus—at the core of the remediation approach can be made of a trench filled with a permeable material packing, which is eventually colonized by the appropriate microorganisms. The bioreactive barrier B is intersecting the contamination plume (FIG. 6a). In order to supply the microbial populations with $H_2$ and $O_2$, as well as C-, N- and P- sources, and mineral salts, the liquid is internally recirculated, passed through the electrolytic cell, and supplemented with the necessary nutrients before being returned to the bioreactive component. The nutrients addition and water electrolysis are regrouped within a fueling electrolytic facility (E in the schematics, in FIG. 6 and following), above ground for practicality of maintenance. The internal liquid recirculation is managed by pumping out the groundwater from a location at the top and on the downstream side of the permeable wall B, and reinjecting it towards several locations at the bottom of the wall on the upstream side, as illustrated in FIG. 7a. Conversely, the extraction well may be placed upfront the biobarrier B (FIG. 7b), such as to maximize the hydraulic gradient between the upstream soil and the biobarrier, and so, the ground water capture efficacy of the funnel or panel; the extracted liquid is reinjected at the bottom of the biocassette (e.g. through a set of horizontal perforated pipes), generating essentially a liquid upflow circulation in the biocassette. Any other configurations are acceptable providing a high turnover of the $H_2$ and $O_2$ enriched liquid is generated upward, to facilitate a fast distribution of the gas species within the overall biological component.

Figure 8A:
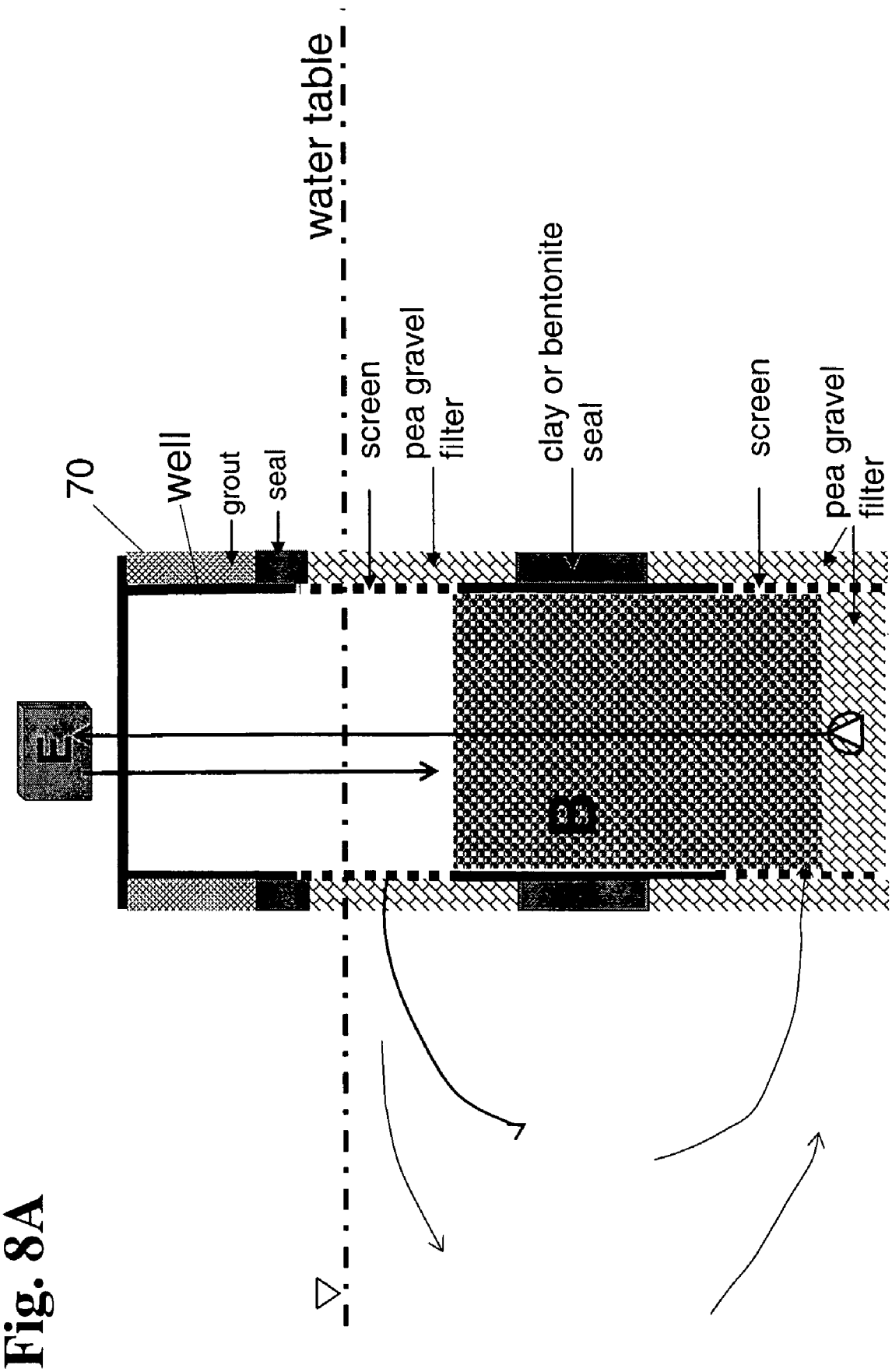
FIG. 8A. Schematics of bioreactive circulating well (not at scale) according to the invention illustrating controllable biological unit that captures the contaminated plume.

In another application, as seen in FIG. 8A, a removeable and replaceable biocassette B can be placed, as a readily controllable biological unit, at the convergence and treatment point ("gate" or "drain") of an impermeable wall system 70 (funnel, panel) that captures the contaminated plume. The bioreactive component B placed at the "gate" (one or several) of an impermeable wall, may have various configurations, such as a circular cartridge (or several ones within a rectangular crib) or a rectangular cartridge, with upward flow of the groundwater together with upflow liquid circulation, or a rectangular cassette with horizontal feeding and tangential passage of the groundwater while the internal circulation is upflow. If retention time has to be magnified, several cassettes and cartridges can be placed in series (sequentially). In order to supply the microbial populations with $H_2$ and $O_2$, as well as C-, N- and P-sources, and mineral salts, the liquid is internally recirculated, passed through the electrolytic cell, and supplemented with the necessary nutrients before being returned to the bioreactive component. The nutrients addition and water electrolysis are regrouped within a fueling electrolytic facility (E in the schematics, in FIG. 8A and following), above ground for practicality of maintenance. The internal liquid recirculation is managed by pumping out the groundwater from a location at the bottom of the biocassette B, and reinjecting it at the top of the biocassette, as illustrated in FIG. 8A. Conversely, the extraction well may be placed upfront the biobarrier B (FIG. 8B-B), such as to maximize the hydraulic gradient between the upstream soil and the biobarrier, and so, the ground water capture efficacy of the funnel or panel; the extracted liquid is reinjected at the bottom of the biocassette (e.g. through a set of horizontal perforated pipes), generating essentially a liquid upflow circulation in the biocassette. Any other configurations are acceptable providing a high turnover of the $H_2$ and $O_2$ enriched liquid is generated upward, to facilitate a fast distribution of the gas species within the overall biological component.

Figure 8B:
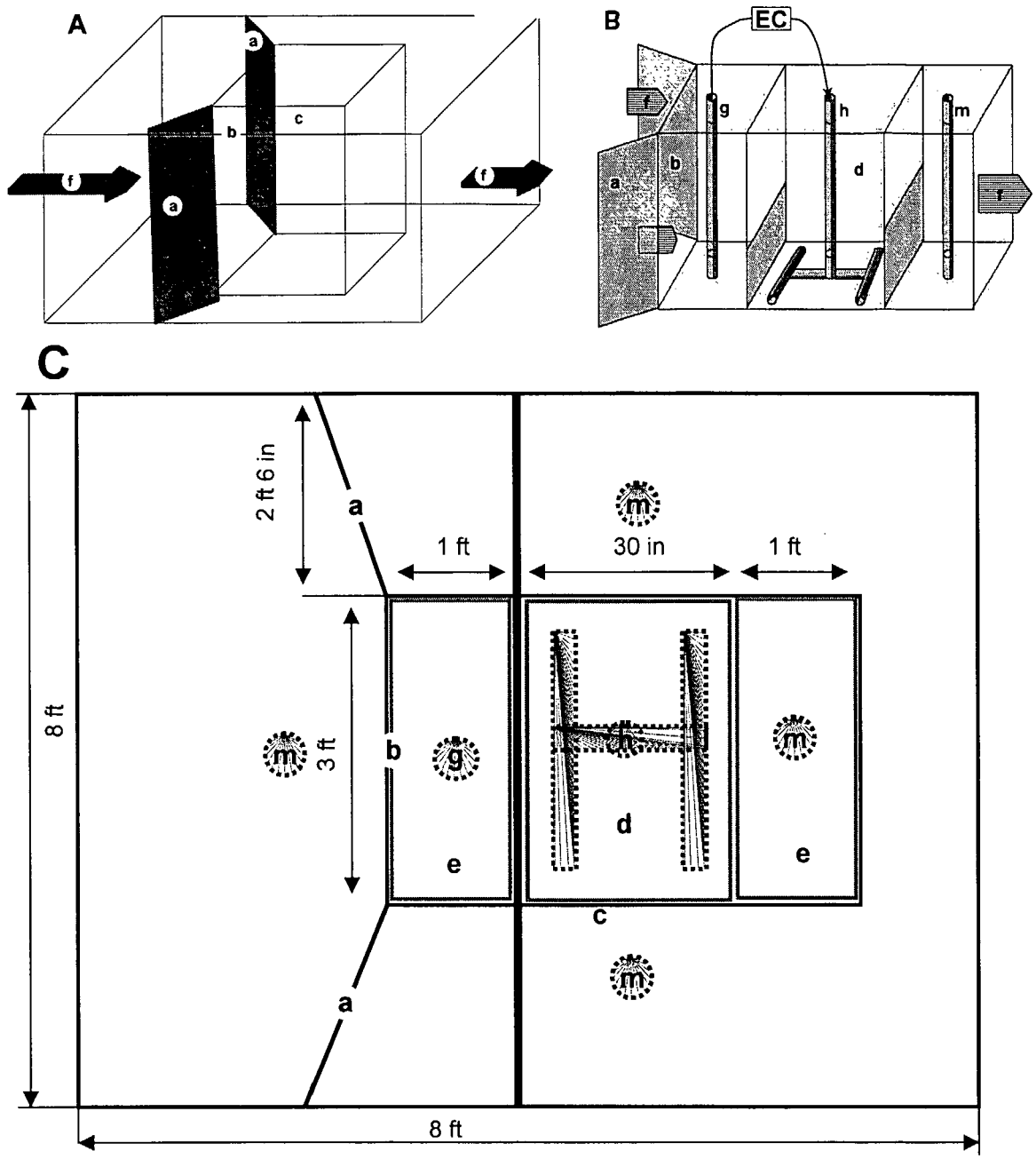
FIG. 8B. eMaMoc application within a permeable reactive barrier system, at pilot-scale in a 8 m3 soil box (A). B, piping details in the barrier at the gate. C, Overview of the box.

An experiment was carried out in a large stainless steel box (2.4 m×2.4 m×1.5 m) (FIG. 8B-A, C) which was filled with coarse sand (sand thickness: approximately 1.2 m). Contaminated groundwater (15-20° C.) was simulated by feeding the box with tap water together with a concentrated PCE aqueous solution (50-70 mg/L) kept in a stainless steel tank, through nine ports evenly distributed on the box wall, using peristaltic pumps. Water was flowing through the box at a linear velocity of ~15 cm/d, with a level of 0.9 m from the floor. The PCE-contaminated plume was captured using a funnel and gate system. The gate frame (caisson) hosted three cassettes (FIG. 8B-B). The first and last cassettes were filled with pea gravel. The middle cassette, removable, was packed with a mixture of peat (bacterial support), volcanic rock (structural support), anaerobic sludge granules and methanotrophic enrichment. The bioactive volume of the cassette was 0.6 m³ (0.9 m width×0.75 m length×0.9 m liquid height). A submersible pump located at bottom of the extraction well, in front of the bioactive cassette was used to recirculate water back to the bioactive cassette via horizontal perforated pipes located at the bottom of the cassette (FIG. 8B-B), so as to maximize the hydraulic gradient between the upstream soil and the barrier, and the groundwater capture efficacy of the funnel. $H_2$ and $O_2$ were generated and transferred to the cassette liquid using an electrolysis cartridge (EC in FIG. 8B-B) placed in the recirculation line. Stock solutions of ethanol (10 g/L) and nutrients (20 g/L fertilizer 20:20:20) were each added to the recirculation line at a rate of 1 L/d (i.e. a solution-to-water ratio in the feed of 1:200, vol./vol.). Carbonated water was introduced into the pre-electrolytic stream of the recirculation loop.

The barrier was operated with an HRT of 4-5 days. The electrical power applied to the electrolytical cartridge (15-20 W) generated oxygen at a flow rate of between 30 and 100 g $O_2/m^3$ reactive barrierd. Dissolved $O_2$ was measured in the circulating liquid as between 1.8 and 3.5 mg/L, and dissolved $CH_4$, between 5 and 12 mg/L. For an influent PCE concentration of 1 to 22 µM (0.2 to 3.7 mg/L), the PCE removal was complete and mineralization fluctuated between 38 and 68% after 40 days of operation, then exceeded 98% after 80 days of operation. The concentrations of PCE, TCE, DCE, and VC in the groundwater downstream from the barrier were inferior to 50 ppb (detection limit). Afterwards incidental increase of the PCE inlet concentration to 85 µM still showed an efficiency removal of over 97%, with effluent concentrations inferior to 50 ppb, for PCE, TCE and DCE, and of 157±33 ppb, for VC. Measurements of inorganic chloride in the inlet and effluent at an influent PCE concentration of 14 mg/L showed a balance of 9±4 mg/L: this means an inorganic chloride-to-PCE chlorine ratio of 75±33% indicating a stoichiometric recovery.

In another application, as seen in FIG. 9 the electrolytic cell 20a is designed and placed in the biocassette B in such a way that the system would be entirely passive (no pump, no liquid cycle; biosystem is fed only by the natural groundwater flow). The electrodes 26, 28 are placed at the bottom of the biocassette B within a well 80, the bottom of which is screened 86, such as they can be retrieved readily for maintenance (cleanup or repair). For that purpose, the electrodes are fixed at one end of a rigid rod (or tube) 82. The tube's extremity at which are fixed the electrodes, is of an external diameter slightly smaller than that of the well and is tapped down such as to have a slope for deflecting the gas laterally. Above the tapped extremity a rubber O-ring 84 (or any other suitable seal) is set around the tube to watertighten the well portion containing the electrode from the rest of the well (FIG. 9*c*). This is to force the gas produced to go laterally out of the well through the screen and spray into the liquid phase of the biosystem. An example of this device implementation is demonstrated within a barrier configuration made of a circular cartridge with upward flow of the groundwater (FIGS. 9*a,b*).

In the case of the dual zone system a singe bioreactive cassette B of cylindrical shape is provided within a rectangular crib, the electrolytic cell 20*b* is designed such as to separate the flux of hydrogen from the flux of oxygen. The anode 28, with a tubular and hollow shape, is surrounded by an interstitial membrane 30 and the cathode 26, also tubular (FIG. 10). The electrolytic cell 20*b* is placed at the bottom of the biosystem, i.e. at the bottom of the anaerobic compartment 22, within a well 60 screened at the bottom. Openings are realized so that all the stream crosses the cell; 95% of the water passes outside the membrane 30 and through the cathode 26 and gets enriched in hydrogen, and gets directed towards the anaerobic compartment 22; while 5% of the liquid stream is carried out inside the anode tube 28, from where, enriched in oxygen, it is directed towards the upper aerobic compartment 24 through a tube prolonging the inner membrane surface. The well 60 is screened at mid-height 62, and above-sealed at 64 to holding pole 65, such as to allow the $O_2$-enriched liquid to leave the well and diffuse within the aerobic compartment from its bottom.

An experiment is being carried out in a pilot-scale stainless steel caisson (0.9 m width×1.4 m length×1.8 m height) containing a two-stage upflow cylindrical biocassette, removable, according to the same schematics as that of FIGS. 10A and B. The bioactive volume of each part (or stage) i.e. the lower part and the upper part, each removable, is 0.29 m$^3$ (0.77 m diameter×0.63 m height). Contaminated groundwater (20-21° C.) was simulated by feeding the caisson with carbonated tap water (130-150 mg $CO_2$/L) together with an ethanol and nutrients solution, and a concentrated PCE aqueous solution (50-70 mg/L), through nine ports evenly distributed on the caisson wall, using peristaltic pumps. The solutions flows-to-water flow ratio were adjusted so to have an inlet concentration (i.e. in front of the anaerobic cassette) of 5 mg PCE/L, 50 mg/L of ethanol-COD, 8 mg/L $NH_4^+$, 3 mg/L phosphate. The lower part of the cassette, removable, was filled with anaerobic sludge granules (280 L at a VSS content of 27 g/L), and the upper part of the cassette, was packed with granulated activated carbon (100 Kg, 56% porosity), and inoculated with methanotrophs-containing activated sludge (140 L at a VSS content of 21 g/L). $H_2$ and $O_2$ were generated and transferred, separately, to the cassette liquid using three two-chamber electrolysis cylindrical probes (as detailed in FIG. 10 C) placed at the bottom of three wells. The biocassette was operated with an HRT of 5 days. The electrical power applied to each electrolytical probe (6 W: 10 V and 0.6 A) generates hydrogen and oxygen, which are diffusing passively in the liquid of the lower and upper compartments, respectively. The results presented below are preliminary, as covering two months of operation. Dissolved $O_2$ was measured at the bottom of the upper cassette as between 1.2 and 3.8 mg/L. Hydrogen is recovered in the off-gas at a flow rate of only 0.15 L/day, as compared to 3 L/d for $CH_4$ and 10 L/d for $O_2$. This indicates that the lower cassette is anaerobically active, as well as the upper aerobic one, methanotrophically active. For an influent PCE concentration of 5 mg/L, the removal of PCE and chlorinated intermediates was complete, after 60 days of operation. The concentrations of PCE, TCE, DCE, and VC in the groundwater downstream from the biocassette are inferior to 50 ppb. The inorganic chlorine balance between the inlet and the effluent is in the order of 6 mg/L; this indicates a stoichiometric recovery of chlorine and that PCE mineralization too should be complete.

In another application, as a particular alternative to the wall approach (either permeable, or impermeable with gates or drains), an array of wells that include a bioreactive component are placed perpendicularly in the path of the contaminated plume. Such a so-called reactive circulation well consists of a double screened well to simultaneously mobilize and treat contaminants from the capillary fringe and the saturated zone. Treatment in the saturated zone is achieved by a combination of soil flushing, and biodegradation in the bioreactor segment (B, in FIG. 10) of the well, filled with MAMO coupled bioparticles (single-stage), or with anaerobic and aerobic bioparticles separately (dual-stage).

FIG. 10 illustrates the standard mode of operation, where groundwater enters the well through the lower screen and leaves through the upper screen. Circulating water is forced through the electrolytic cell, to enrich it in $H_2$ and $O_2$, and appropriate nutrients (E, electrolytic fueling unit, in FIG. 8A). In the reverse circulation mode, groundwater enters the well through the upper screen and leaves through the lower screen.

In another application, a setup of extraction and injection wells can be used to transform a part of aquifer between the injection and extraction wells in a bioreactive zone by promoting microbial growth (either of indigeneous or added populations) of methanogenic and methanotrophic populations due to the presence of hydrogen and oxygen, produced by the electrolysis cell placed on the path of the water circulation between the extraction and injection wells 90 and 92 (FIG. 11). In an alternative application, extraction and injection wells can be placed such as have a downflow biofiltration bed in the vadose zone, (FIG. 12), above the contamination source or any area required to be cleaned. The circulation of the extracted water is downflow through the biobed. The circulating water also is supplied in $H_2$ and $O_2$ produced by the electrolysis cell (not shown) placed also on the path of the water circulation between the extraction and injection wells.

Overall, the proposed method of hydrogen and oxygen supply to aquifer can be used in a variety of configurations aimed at combined anaerobic-aerobic biodegradation.

REFERENCES

Amaral, J. A., and R. Knowles. 1995. Growth of methanotrophs in methane and oxygen counter gradient. FEMS Microbiology Letters. 126:215-220.

Beunink, J. and Rehm, H. J. 1990. Coupled reductive and oxidative degradation of 4-chloro-2-nitrophenol by a co-immobilized mixed culture system. Appl. Microbiol. Biotechnol., 34: 108-115.

Brown, J. F. J., Bedard, D. L., Brennan, M. J., Carnahan, J. C., Feng, H. and Wagner, R. 1987. Polychlorinated biphenyl dechlorination in aquatic sediments. Science, 236: 709-712.

Felekea Z., and Y. Sakakibarab. 2002. A bio-electrochemical reactor coupled with adsorber for the removal of nitrate and inhibitory pesticide. Water Research, 36:3092-3102.

Field, J. A., Stams, A. J. M., Kato, M., and Schraa, G. 1995. Enhance biodegradation of aromatic pollutants in cocultures of anaerobic and aerobic bacterial consortia. A. van Leeuwenhoek, 67: 47-77.

Franz, J. A., R. J. Williams, J. R. V. Flora, M. E. Meadows, W. G. Irwin. 2002. Electrolytic oxygen generation for subsurface delivery:effects of precipitation at the cathode and an assessment of side reactions. Water Research, 36:2243-2254.

Galli, R. and McCarty, P. L. 1989. Biotransformation of 1,1, 1-trichloroethane, trichloromethane, and tetrachloromethane by a *Clostridium* sp. Appl. Environ. Microbiol., 55: 837-844.

Guiot, S. R. 1997a. Anaerobic and aerobic integrated system for biotreatment of toxic wastes (CANOXIS)" U.S. Pat. No. 5,599,451, Feb. 4, 1997.—Canada Patent No. 2,133.265, Jan. 8, 2002.

Guiot, S. R. 1997b. Process coupling of anaerobic and aerobic biofilms for treatment of contaminated waste liquids." In: D. L. Wise (Ed.), Global Environmental Biotechnology: proc. Int. Symp. (3rd: 1996: Boston, Mass. USA) of the Int. Society for Environ. Biotech. (Studies in Environmental Sciences vol. 66), Elsevier Science, Amsterdam, pp. 591-601 (ISBN 0-444-82534-7).

Janssen, D. B., van den Wijngaard, A. J., van der Waarde, J. J. and Oldenhuis, R. 1991. Biochemistry and kinetics of aerobic degradation of chlorinated aliphatic hydrocarbons. In: Proc. of the On-site bioreclamation—Processes for xenobiotic and hydrocarbon treatment, Hinchee, R. E. and Olfenbuttel, R. F. (Ed.), Butterworth-Heinemann, Boston, Mass., USA, pp. 92-112.

Major D., Edwards E., McCarty P., Gossett J., Hendrickson H., Loeffler F., Zinder S., Ellis D., Vidumsky J., Harkness M., Klecka G. and Cox E. 2003. Discussion of Environment vs. Bacteria or Let's play, 'Name that Bacteria'. Ground Water Monitoring & Remediation, 23(2): 32-38.

Miguez C. B., Shen C. F., Bourque D., Guiot S. R. and Groleau D. 1999. Monitoring methanotrophic bacteria in hybrid anaerobic-aerobic reactors using PCR and a catabolic gene probe. Appl. Env. Microbiol. 65: 381-388

Mohn, W. W. and Tiedje, J. M. 1992. Microbial reductive dehalogenation. Microbiol. Rev., 56: 482-507.

Pauss, A., G. Andre, M. Perrier, and S. R. Guiot. 1990. Liquid-to-gas mass transfer in anaerobic processes: inevitable transfer limitations of methane and hydrogen in the biomethanation process. Appl. Environ. Microbiol., 56:1336-1344.

Tartakovsky B., Sheintuch M. and Guiot S. R. 1998. Modeling and analysis of co-immobilized aerobic/anaerobic mixed cultures. Biotech. Progress, 14: 672-679.

Tartakovsky B., A. Michotte, J-C. A. Cadieux, P. C. K. Lau, J. A. Hawari and S. R. Guiot 2001a. Degradation of polychlorinated biphenyls in a single stage anaerobic/aerobic bioreactor. Water Research, 35: 4323-4330.

Tartakovsky, B., M.-F. Manuel and S. R. Guiot. 2003. Trichloroethylene degradation in a coupled aerobic/anaerobic reactor oxygenated using hydrogen peroxide. Env. Sci. & Techn. 37(24): 5823-5828.

Zitomer, D. H. and Speece, R. E. 1993. Sequential environments for enhanced biotransformation of aqueous contaminants. Environ. Sci. Technol., 27: 227-244.

The invention claimed is:

1. A method for continuous synchronous bioremediation of an aqueous contaminated liquid including a contaminant requiring reductive and oxidative steps for its biodegradation, comprising
    (a) providing a bioreactor containing a coupled single phase anaerobic(methanogenic)/aerobic(methanotrophic) biofilm, said biofilm comprising an anaerobic (methanogenic) zone located at a central core area of the biofilm, and a juxtaposed aerobic (methanotrophic) zone at a surrounding peripheral area of the biofilm, in fluid communication with the anaerobic (methanogenic) zone, and including a decreasing gradient of oxygen concentration from the aerobic (methanotrophic) zone to the anaerobic (methanogenic) zone toward the core area, and an electrolytic cell for hydrolyzing water to produce dissolved oxygen and hydrogen, in fluid communication with the bioreactor,
    (b) circulating the contaminated liquid through the electrolytic cell to together introduce a controlled amount of dissolved oxygen and hydrogen into the contaminated liquid, and
    (c) continuously cycling the oxygenated and hydrogenated contaminated liquid produced in step (b) through the bioreactor, wherein dissolved hydrogen is used as an electron donor by methanogenic bacteria and to in situ generate methane, and by anaerobic bacteria including methanogens; and dissolved oxygen is used as an electron acceptor by aerobic, including methanotrophic bacteria, and methane is used by methanotrophic bacteria, to remediate the contaminated liquid, respectively by synchronous reductive and oxidative steps.

2. A method according to claim 1, wherein the amount of oxygen dissolved in said contaminated liquid is adjusted to the rate of oxygen consumption by the biofilm.

3. A method according to claim 1, wherein the contaminated liquid is ground water.

4. A method according to claim 1, wherein the contaminated liquid comprises contaminants which include those which are reductively degradable by anaerobic bacteria to forms which are further oxidatively degradable by aerobic bacteria to non-toxic forms.

5. A method according to claim 4, wherein the contaminants include highly chlorinated organic compounds.

6. A method for continuous synchronous bioremediation of an aqueous contaminated liquid including a contaminant requiring reductive and oxidative steps for its biodegradation, comprising
    (a) providing a bioreactor containing a coupled dual phase anaerobic(methanogenic) aerobic(methanotrophic) biofilm, said biofilm comprising a layer of an aerobic (methanotrophic) zone spatially distant from and in fluid communication at an interface with a layer of an anaerobic (methanogenic) zone, and including a decreasing gradient of oxygen concentration from the aerobic (methanotrophic) zone to the anaerobic (methanogenic) zone, and an electrolytic cell for hydrolyzing water to produce dissolved oxygen and hydrogen, in fluid communication with the bioreactor,
    (b) circulating the contaminated liquid through the electrolytic cell to introduce a controlled amount of dissolved oxygen into a stream of the contaminated liquid and a controlled amount of dissolved hydrogen into another stream of the contaminated liquid, and providing dissolved oxygen to the aerobic (methanotrophic) zone and dissolved hydrogen to the anaerobic (methanogenic) zone, and
    (c) continuously cycling the oxygenated and hydrogenated contaminated liquid produced in step (b) through the bioreactor, wherein dissolved hydrogen is used as an electron donor by methanogenic bacteria and to in situ generate methane, and by anaerobic bacteria including methanogens; and dissolved oxygen is used as an electron acceptor by aerobic, including methanotrophic bacteria and methane is used by methanotrophic bacteria, to remediate the contaminated liquid, respectively by synchronous reductive and oxidative steps.

7. A method according to claim 6, wherein the amount of oxygen dissolved in said contaminated liquid is adjusted to the rate of oxygen consumption by the biofilm.

8. A method according to claim 6, wherein the contaminated liquid is ground water.

9. A method according to claim 6, wherein the contaminated liquid comprises contaminants which include those which are reductively degradable by anaerobic bacteria to forms which are further oxidatively degradable by aerobic bacteria to non-toxic forms.

10. A method according to claim 9, wherein the contaminants include highly chlorinated organic compounds.

* * * * *